US009113861B2

(12) United States Patent
Martin et al.

(10) Patent No.: US 9,113,861 B2
(45) Date of Patent: Aug. 25, 2015

(54) ARTICULATING NEEDLE DRIVER

(75) Inventors: David T. Martin, Milford, OH (US);
James A. Woodard, Jr., Mason, OH (US); Carl J. Shurtleff, Mason, OH (US); Andrew C. Yoo, Cinicinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 66 days.

(21) Appl. No.: 13/466,188

(22) Filed: May 8, 2012

(65) Prior Publication Data

US 2012/0289975 A1 Nov. 15, 2012

Related U.S. Application Data

(60) Provisional application No. 61/484,395, filed on May 10, 2011.

(51) Int. Cl.
*A61B 17/062* (2006.01)
*A61B 17/04* (2006.01)
*A61B 17/29* (2006.01)

(52) U.S. Cl.
CPC ........... *A61B 17/062* (2013.01); *A61B 17/0469* (2013.01); *A61B 17/0483* (2013.01); *A61B 2017/2926* (2013.01)

(58) Field of Classification Search
CPC ............. A61B 17/062; A61B 17/0469; A61B 17/0483; A61B 2017/2926
USPC ........................... 606/139, 144, 147, 148, 145
See application file for complete search history.

(56) References Cited

U.S. PATENT DOCUMENTS

| | | | | |
|---|---|---|---|---|
| 5,304,185 A | * | 4/1994 | Taylor | 606/147 |
| 5,413,583 A | | 5/1995 | Wohlers | |
| 5,556,402 A | * | 9/1996 | Xu | 606/147 |
| 5,562,702 A | * | 10/1996 | Huitema et al. | 606/207 |
| 5,643,294 A | * | 7/1997 | Tovey et al. | 606/148 |
| 5,704,534 A | * | 1/1998 | Huitema et al. | 227/175.1 |
| 5,951,575 A | * | 9/1999 | Bolduc et al. | 606/144 |
| 5,951,587 A | * | 9/1999 | Qureshi et al. | 606/207 |
| 6,056,771 A | | 5/2000 | Proto | |
| 6,171,316 B1 | * | 1/2001 | Kovac et al. | 606/144 |
| 6,270,508 B1 | * | 8/2001 | Klieman et al. | 606/147 |
| 6,663,641 B1 | * | 12/2003 | Kovac et al. | 606/144 |
| 8,137,339 B2 | | 3/2012 | Jinno et al. | |

(Continued)

FOREIGN PATENT DOCUMENTS

EP           0571057 A1 *  11/1993 ............. A61B 17/28

*Primary Examiner* — Julian W Woo
*Assistant Examiner* — Lucas Paez
(74) *Attorney, Agent, or Firm* — Frost Brown Todd LLC

(57) ABSTRACT

A needle holder includes a shaft and a needle driver located at the distal end of the shaft. The needle driver is operable to rotate a needle such that the needle forms a non-perpendicular angle with a longitudinal axis of the shaft. In some versions, the needle driver includes a first arm and a rotatable assembly that is configured to longitudinally clamp about a portion of a needle. The rotatable assembly may include self-righting features to right the needle perpendicular to the first arm. The needle driver may further include a second arm that is pivotable relative to the first arm. The rotatable assembly may include a top member associated with the second arm and a bottom member associated with the first arm. In some versions, spring-loaded collets may secure the needle to a rotatable assembly. Alternatively, a pair of actuating arms may pivot the needle about a curved surface.

20 Claims, 15 Drawing Sheets

(56) References Cited

U.S. PATENT DOCUMENTS

| | | | |
|---|---|---|---|
| 2009/0228025 A1* | 9/2009 | Benson | 606/144 |
| 2010/0076461 A1* | 3/2010 | Viola et al. | 606/144 |
| 2010/0100125 A1 | 4/2010 | Mahadevan | |
| 2012/0123471 A1 | 5/2012 | Woodard, Jr. et al. | |

* cited by examiner

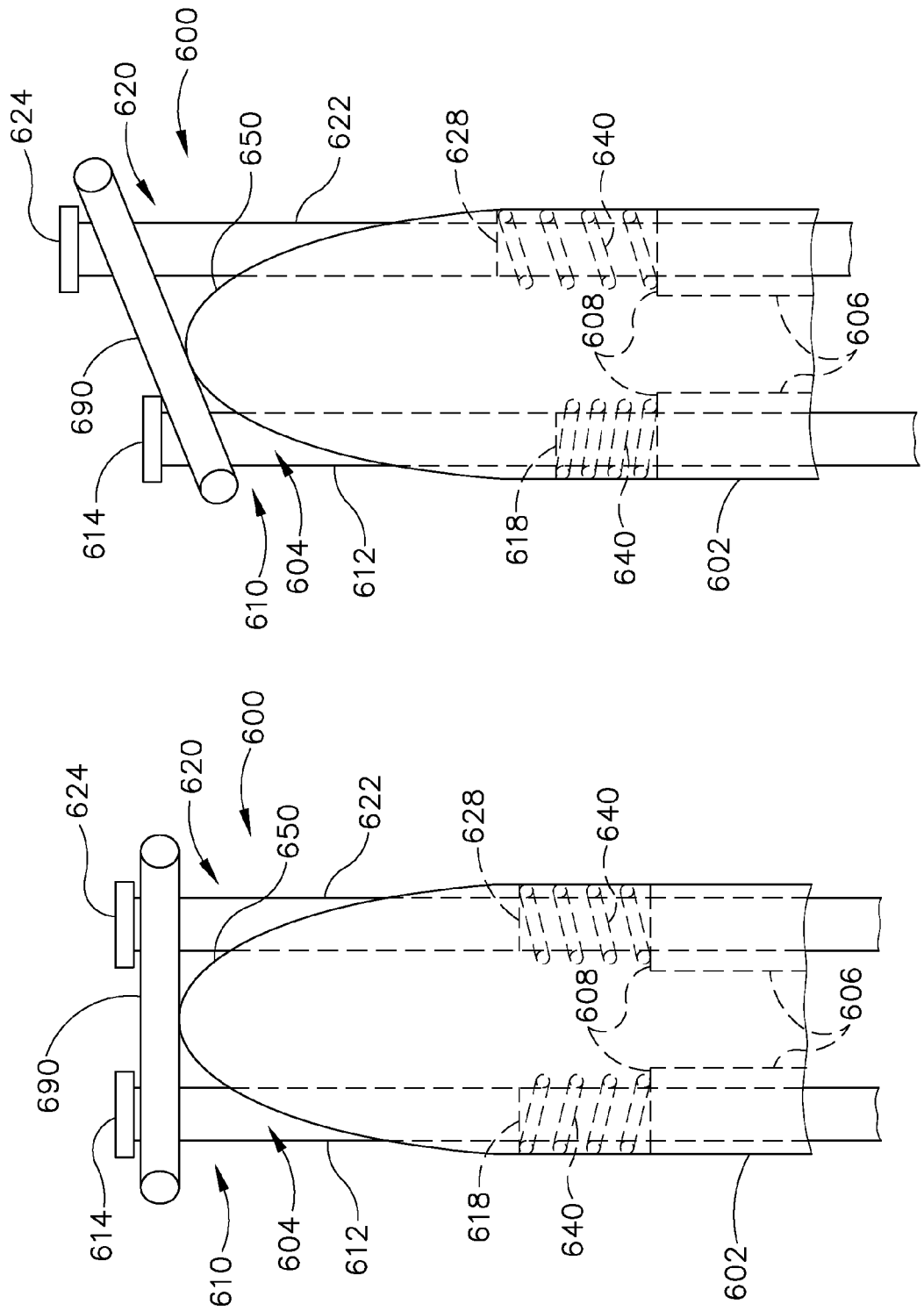

ARTICULATING NEEDLE DRIVER

PRIORITY

This application claims priority to U.S. Provisional Application Ser. No. 61/484,395, filed May 10, 2011, entitled "Laparoscopic Suturing Devices and Methods," the disclosure of which is incorporated by reference herein.

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparoscopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Needle holders may be used to grasp and maneuver a needle during suturing operations through the use of a fixed arm and a grasping arm that clamp about a needle. Thus, a user can grasp, maneuver, and release a needle between the fixed arm and grasping arm. In some versions, the holders may include a self-righting feature to rotate the needle into a position that is perpendicular to both the longitudinal axis of the needle holder and to the arm surfaces when clamped. Merely exemplary needle holders are disclosed in U.S. Pat. No. 5,413,583, entitled "Force Limiting Arrangement for Needle Holder for Endoscopic Surgery," issued May 9, 1995 and U.S. Pat. No. 5,951,587, entitled "Needle Holder with Suture Filament Grasping Abilities," issued Sep. 14, 1999, the disclosures of which are incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, entitled "Custom Needle for Suture Instrument," filed Nov. 15, 2010, the disclosure of which is incorporated by reference herein; and U.S. patent application Ser. No. 13/295,186, entitled "Needle for Laparoscopic Suturing Instrument," filed on Nov. 14, 2011, published as U.S. Pub. No. 2012/012347 on May 17, 2012, the disclosure of which is incorporated by reference herein.

While several systems and methods have been made and used for laparoscopic suturing devices, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 13A depicts a top view of still another exemplary needle driver having a pair of arms and a curved bearing surface and shown grasping a needle in a first position; and FIG. 13B depicts a top view of the needle driver of FIG. 13A showing the needle rotated about the bearing surface to a second position.

Figure 1:
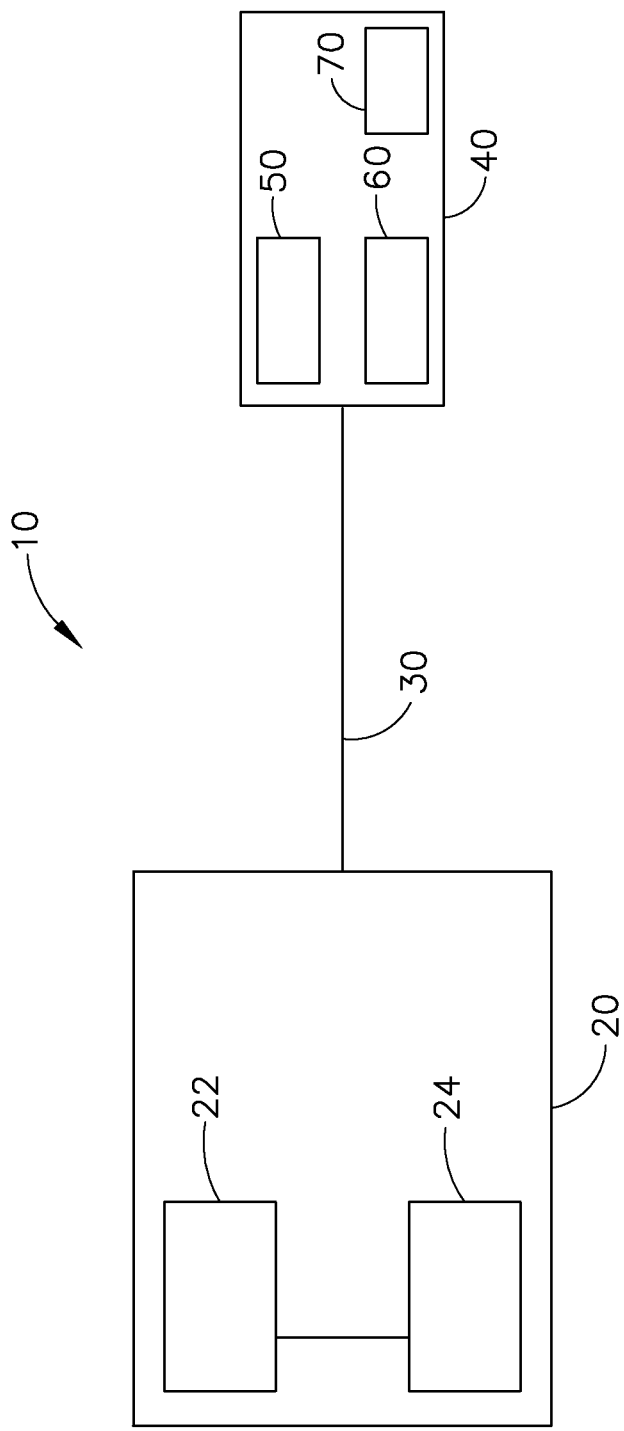
FIG. 1 depicts a block schematic diagram of an exemplary needle holder.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 depicts a block schematic view of an exemplary needle holder (10) having a body portion (20), a shaft (30) extending distally from the body portion (20), and a needle driver (40) coupled to a distal end of shaft (30). In the present example, body portion (20) comprises a trigger (22) and a toggle (24). Trigger (22) is operable to rotate a grasping arm (50) relative to a stationary arm (60), as will be described in greater detail below. In some versions, trigger (22) comprises a first handle that is rotatable fixed relative to shaft (30) and a second handle that is rotatable relative to shaft (30) and the first handle such that rotation of the second handle is operable to rotate grasping arm (50). In some versions, a ratchet feature may be provided to ratchet the second handle relative to the first handle. In other versions, trigger (22) may include a longitudinal slider. Such a slider may be actuated proximally and/or distally relative to body portion (20). In some versions, a spring may be provided to bias trigger (22) to a first, unactuated position. Of course still further configurations for trigger (22) will be apparent to one of ordinary skill in the art in view of the teachings herein.

Toggle (24) of the present example is operable to rotate or otherwise control an articulation assembly (70), as will also be described below. In some versions toggle (24) comprises a rotatable knob. Such a knob may include a ratcheting feature and/or a spring to bias the knob to a first, unactuated position. In other versions, toggle (24) may include a longitudinal slider. Such a slider may be actuated proximally and/or distally relative to body portion (20). In some versions, a spring may be provided to bias toggle (24) to the first, unactuated position. Still other configurations for toggle (24) will be apparent to one of ordinary skill in the art in view of the teachings herein.

Shaft (30) extends distally from body portion (20) and is coupled to needle driver (40). In the present example, shaft (30) comprises a hollow cylindrical member having one or more linkages (not shown) therein. Such linkages mechanically couple features of body portion (20) to needle driver (40). By way of example only, trigger (22) may be coupled to grasping arm (50) via one or more rods, cables, struts, belts, and/or any other mechanical linkages as will be apparent to one of ordinary skill in the art in view of the teachings herein. Of course, it should be understood that, in some versions, wiring may extend through shaft (30) such that a position sensor (not shown) coupled to trigger (22) may be used to control a motor, servo, or other member located in shaft (30) and/or needle driver (40) to rotate grasping arm (50) relative to stationary arm (60). Still other configurations will be apparent to one of ordinary skill in the art in view of the teachings herein. Likewise, toggle (24) may be coupled to articulation assembly (70) via one or more rods, cables, struts, belts, and/or any other mechanical linkages as will be apparent to one of ordinary skill in the art in view of the teachings herein. It should be understood that, in some versions, wiring may extend through shaft (30) such that a position sensor (not shown) coupled to toggle (24) may be used to control a motor, servo, or other member located in shaft (30) and/or needle driver (40) to rotate articulation assembly (70) relative to stationary arm (60). Still other configurations will be apparent to one of ordinary skill in the art in view of the teachings herein.

As described above, needle driver (40) of the present example is coupled to a distal end of shaft (30), though this is merely optional. In some versions, needle driver (40) may be directly coupled to body portion (20). Needle driver (40) of the present example comprises a grasping arm (50), a stationary arm (60), and an articulation assembly (70). Grasping arm (50) of the present example is pivotably coupled to shaft (30) and is rotatable relative to stationary arm (60) such that grasping arm (50) and stationary arm (60) may cooperatively grasp an object, such as a needle, tissue or otherwise, when grasping arm (50) is pivoted to a closed position from an open position. In some versions, grasping arm (50) may be pivotably coupled to stationary arm (60) instead of shaft (30). A proximal end of grasping arm (50) of the present example is coupled to a linkage (not shown) such that trigger (22) may rotate grasping arm (50) relative to stationary arm (60). Stationary arm (60) of the present example is fixedly coupled to shaft (30) so as to provide a mechanical ground for grasping arm (50) and/or articulation assembly (70). In the present example, articulation assembly (70) is associated with stationary arm (60), though this is merely optional. In some versions, portions of articulation assembly (70) may be associated with both grasping arm (50) and stationary arm (60) and/or solely with grasping arm (50). Articulation assembly (70) is operable to rotate a needle (not shown) relative to grasping arm (50) and/or stationary arm (60) such that a user may adjust the orientation of the needle. In the present example, such rotation is about a vertical axis extending vertically through stationary arm (60) and perpendicular to a longitudinal axis of needle holder (10). Of course other configurations for needle driver (40) will be apparent to one of ordinary skill in the art in view of the teachings herein. For example, in some versions, grasping arm (50), stationary arm (60), and/or articulation assembly (70) may include a self-righting feature that rotates the needle into a perpendicular, vertical position relative to needle driver (40). Needle holder (10) may be further constructed in accordance with at least some of the teachings of U.S. Pat. No. 5,413,583, entitled "Force Limiting Arrangement for Needle Holder for Endoscopic Surgery," issued May 9, 1995 and/or U.S. Pat. No. 5,951,587, entitled "Needle Holder with Suture Filament Grasping Abilities," issued Sep. 14, 1999, the disclosures of which are incorporated by reference herein.

Initially a user locates the needle between grasping arm (50) and stationary arm (60) and operates trigger (22) to capture the needle between grasping arm (50) and stationary arm (60). If a self-righting feature is incorporated into needle driver (40), the needle may be self-righted as arms (50, 60) close about the needle. With the needle grasped by arms (50, 60) the user operates toggle (24) to rotate the needle about the vertical axis and relative to arms (50, 60) to a desired rotational orientation. The user can then insert the needle through tissue by rotating or otherwise manipulating needle holder (10). A second needle holder (not shown) may be used in conjunction with needle holder (10), though this is merely optional and may be omitted. In some versions, the second needle holder may be configured in substantially the same manner as needle holder (10) or may be configured in any other manner. The user may grasp the needle with the second needle holder. The user then releases trigger (22) to release the needle from needle driver (40). As noted above, a spring may be provided to bias trigger (22) to the first, unactuated position to release the needle. The user may manipulate the second needle holder to pull the needle and an attached suture through the tissue after the needle is released from needle holder (10). The user may then regrasp the needle with needle holder (10) and repeat the above process to continue a suturing operation.

Shaft (30) of the present example has an outer diameter sized to permit assembly (30) to be inserted through a conventional trocar (not shown). Shaft (30) also has a length sized to permit needle driver (40) to be positioned at a surgical site within a patient while also allowing body portion (20) to be manipulated by a user (e.g., a surgeon) from a location outside the patient when shaft (30) is disposed in a trocar. Of course, shaft (30) need not necessarily be dimensioned for use through a trocar. For instance, needle holder (10) may be used and/or configured for use in open surgical procedures.

II. Exemplary Needle Drivers with Articulation Assemblies

As described above, articulation assembly (70) is operable to rotate a needle relative to grasping arm (50) and stationary arm (60) such that the orientation of the needle may be adjusted. In particular, in examples where the needle is a curved needle and lies along a needle plane, articulation assembly (70) is operable to rotate that needle plane relative to grasping arm (50) and stationary arm (60) to orient the needle plane at angles that are oblique relative to the longitudinal axis of shaft (30). In the present example, this rotation of the needle plane is provided about needle plane axis of rotation that is perpendicular to the longitudinal axis of shaft (30). This needle plane axis of rotation may remain perpendicular to the longitudinal axis of shaft (30) as the needle plane is rotated to various orientations that are oblique relative to the longitudinal axis of shaft (30).

In some instances, needle driver (40) may initially receive the needle in an orientation where the needle plane axis of rotation would be non-perpendicular relative to the longitudinal axis of shaft (30). In some such instances, needle driver (40) is operable to "right" the needle by automatically rotating the needle about a needle righting axis as grasping arm (50) is moved toward stationary arm (60) to grasp the needle. This needle righting axis may be perpendicular to the needle plane rotation axis. This "righting" about the needle righting axis may ultimately position the needle plane rotation axis perpendicular to the longitudinal axis of shaft (30) when arms (50, 60) sufficiently grasp the needle. Various examples for articulation assembly (70) and/or needle driver (40) will be described in greater detail below, while still other suitable examples will be apparent to those of ordinary skill in the art in view of the teachings herein.

A. Exemplary Rotating Puck Articulation Assembly

Figure 2:
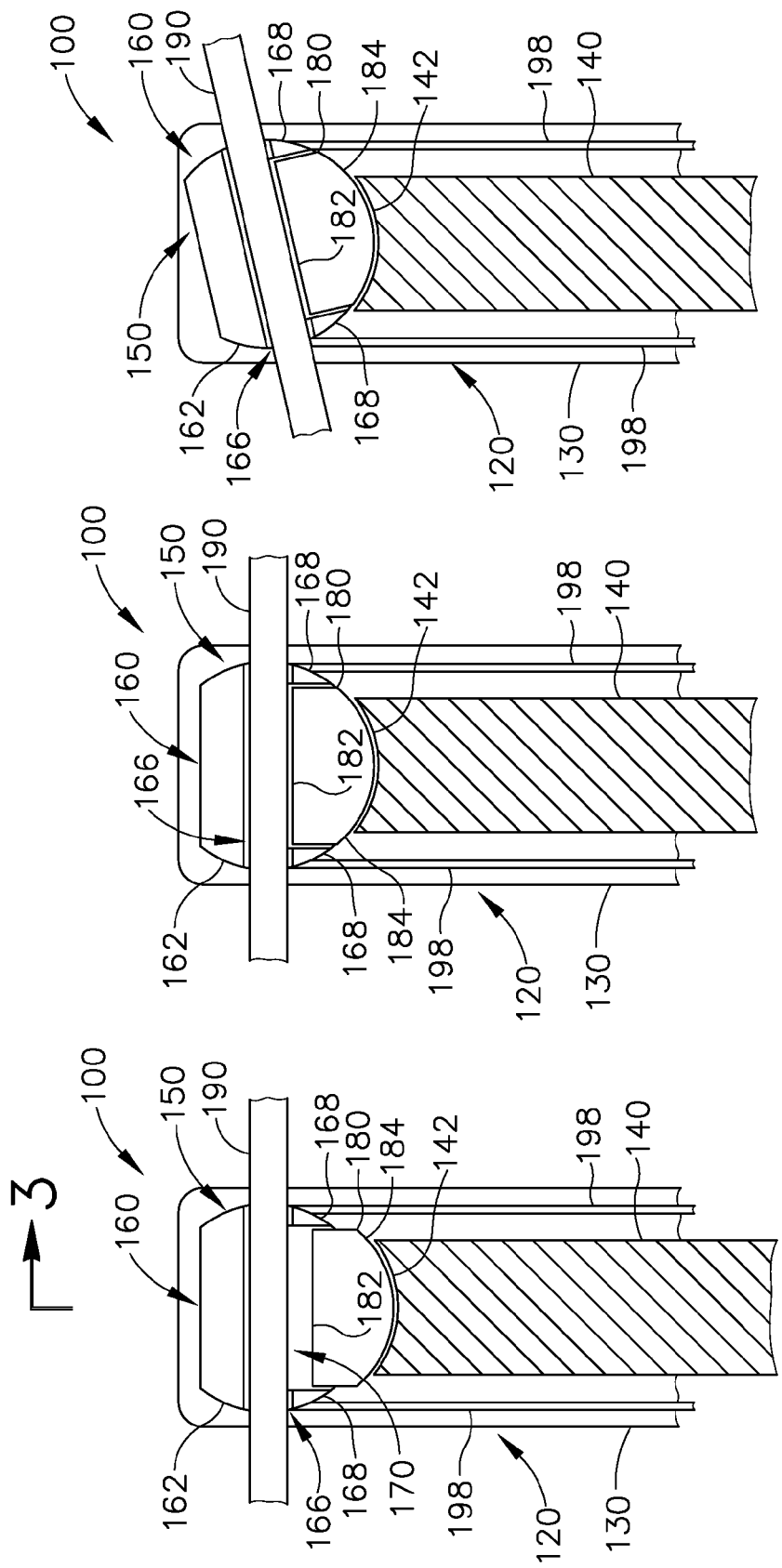
FIG. 2A depicts a top view of an exemplary needle driver with a grasping arm removed and showing a rotating puck assembly in an open position.
FIG. 2B depicts a top view of the needle driver of FIG. 2A showing the rotating puck assembly in a closed position.
FIG. 2C depicts a top view of the needle driver of FIG. 2A showing the rotating puck assembly in a rotated position.
Figure 3:
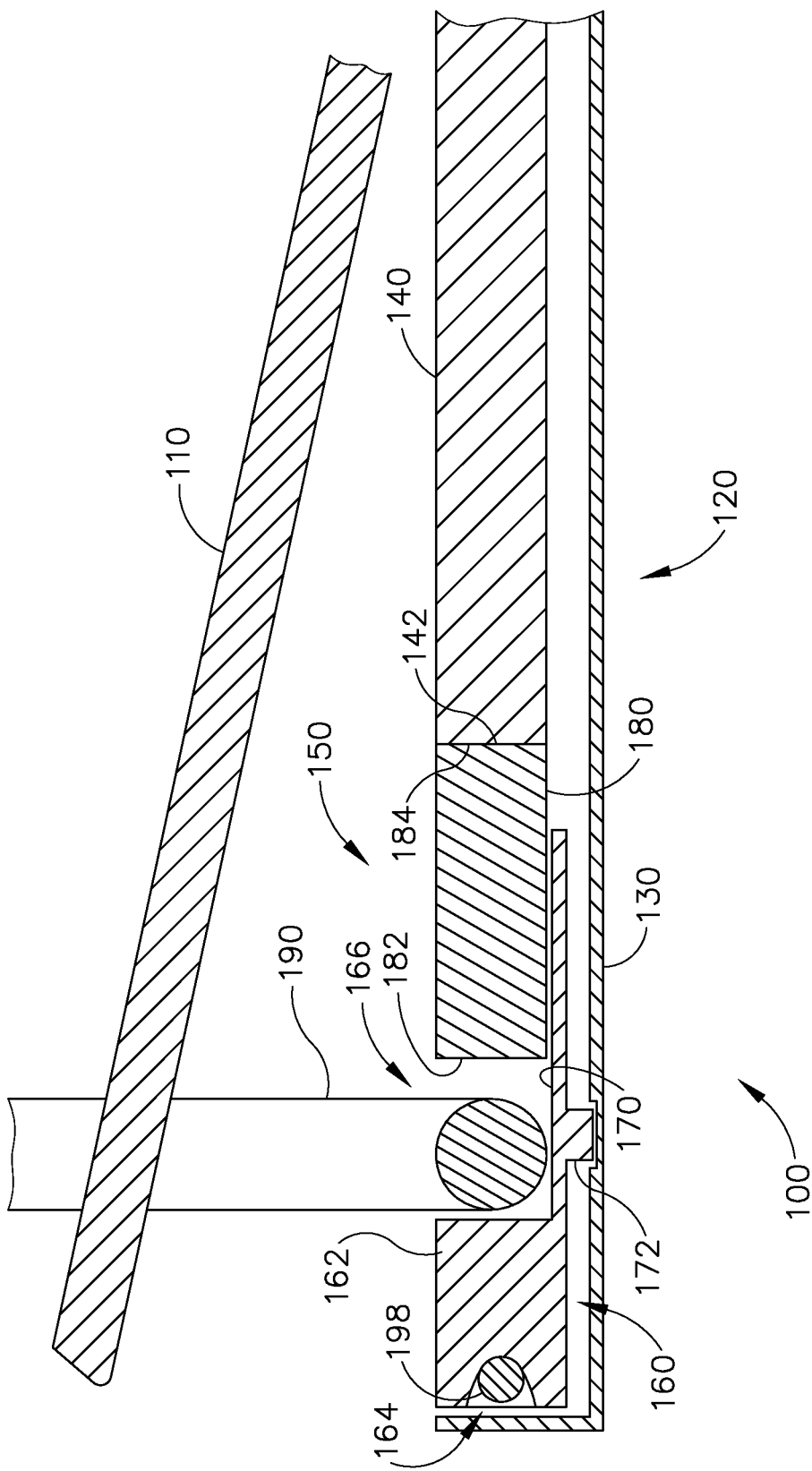
FIG. 3 depicts a side elevation cross-sectional view of the needle driver of FIG. 2A taken along section line 3-3.

FIGS. 2A-3 depict a merely exemplary articulation assembly for an exemplary needle driver (100) for a needle holder that comprises a rotating puck assembly (150). Referring initially to FIG. 3, needle driver (100) comprises a grasping arm (110) and a stationary arm (120). Grasping arm (110) is pivotable relative to stationary arm (120) via a trigger (not shown), such as trigger (22). In some versions, grasping arm (110) is pivotably coupled to a shaft (also not shown), such as shaft (30), or grasping arm may be pivotably coupled to stationary arm (120). Grasping arm (110) of the present example is operable to substantially vertically contain a needle (190) between grasping arm (110) and stationary arm (120) such that a user may maneuver needle (190) with the needle holder. Needle (190) may be constructed in accordance with at least some of the teachings of U.S. Pat. No. 6,056,771, entitled "Radiused Tip Surgical Needles and Surgical Incision Members," issued May 2, 2000; U.S. Pub. No. 2010/0100125, entitled "Suture Needle and Suture Assembly," published Apr. 22, 2010; U.S. Provisional Application Ser. No. 61/413,680, entitled "Custom Needle for Suture Instrument," filed Nov. 15, 2010; U.S. patent application Ser. No. 13/295,186, entitled "Needle for Laparoscopic Suturing Instrument," filed on Nov. 14, 2011, published as U.S. Pub. No. 2012/0123471 on May 17, 2012, the disclosures of which are incorporated by reference herein; and/or in any other manner as will be apparent to one of ordinary skill in the art in view of the teachings herein.

It should be understood that grasping arm (110) of the present example does not tightly grip needle (190) against stationary arm (120). Rather, puck assembly (150) longitudinally clamps needle (190) to substantially secure needle (190) relative to stationary arm (120), as will be described in greater detail below. Grasping arm (110) may be formed of metal (such as stainless steel), thermoplastic, and/or any other material or combination of materials as will be apparent to one of ordinary skill in the art. It should be understood that grasping arm (110) may also incorporate additional features, such as ridging, friction padding, suture cutting features, and/or other features as will be apparent to one of ordinary skill in the art in view of the teachings herein. In some versions, grasping arm (110) may be omitted entirely.

Still referring to FIG. 3, stationary arm (120) comprises a base (130), rotating puck assembly (150), and a pushing member (140). Base (130) of the present example may be formed of metal (such as stainless steel), thermoplastic, and/ or any other material or combination of materials as will be apparent to one of ordinary skill in the art. Similar to grasping arm (110), it should be understood that stationary arm (120)

may incorporate additional features, such as ridging, friction padding, suture cutting features, and/or other features as will be apparent to one of ordinary skill in the art in view of the teachings herein. In some versions, a cover member (not shown) may be included atop stationary arm (120) to enclose pushing member (140) therein. In a further version, such a cover member may include an opening such that a portion of puck assembly (150) is exposed through the cover member while a portion of puck assembly (150) is enclosed between the cover member and base (130). Of course still further configurations for base (130) and/or the cover member will be apparent to one of ordinary skill in the art in view of the teachings herein.

Puck assembly (150) of the present example comprises a rotatable member (160) and a compression member (180). Rotatable member (160) includes a distal protrusion (162), a needle recess (166), and a pivot (172). Distal protrusion (162) provides a surface against which needle (190) is compressed when compression member (180) is longitudinally actuated by pushing member (140), as will be described in greater detail below. In some versions, distal protrusion (162) and needle (190) may include self-righting features (for example, complementary flat and/or curved portions), such that needle (190) is substantially perpendicularly oriented relative to stationary arm (120) when compression member (180) compresses needle (190) against distal ledge (162). In addition, or in the alternative, compression member (180) may likewise include self-righting features (for example, complementary flat and/or curved portions), such that needle (190) is substantially perpendicularly oriented relative to stationary arm (120) when compression member (180) compresses needle (190) against distal protrusion (162). In some versions, distal protrusion (162) and/or a portion of distal protrusion (162) may be formed of a resilient material such that needle (190) deforms the resilient material when compressed by compression member (180), though this is merely optional and may be omitted. Of course distal protrusion (162) may have other configurations, as will be apparent to one of ordinary skill in the art in view of the teachings herein.

Needle recess (166) is operable to receive needle (190) therein. A pair of proximal protrusions (168), shown in FIGS. 2A-2C, provide a proximal end for needle recess (166) and horizontally retain compression member (180) atop a ledge (170). In the present example, proximal protrusions (168) and a proximal end (184) of compression member (180) form a substantially curved interface, as will be described in greater detail below. Ledge (170) extends proximally from needle recess (166) and between proximal protrusions (168) of rotatable member (160) to form a surface upon which compression member (180) is supported and retained. A pivot (172) extends downwardly from a bottom surface of rotatable member (160) to pivotably couple rotatable member (160) to base (130). Pivot (172) may simply comprise a protrusion that is mounted within a recess formed in base (130) such that rotatable member (160) can rotate relative to base (130). In some versions, ball bearings or other rotation members may be used to couple and permit rotation of rotatable member (160) relative to base (130). Still other configurations will be apparent to one of ordinary skill in the art in view of the teachings herein.

As shown in FIG. 3, compression member (180) sits atop ledge (170) and is longitudinally actuatable relative to rotatable member (160) via pushing member (140). Referring to FIG. 2A, compression member (180) comprises a distal end (182) and a proximal end (184). In some versions, distal end (182) may simply comprise a flat face that compresses needle (190) against distal protrusion (162) of rotatable member (160). Of course, in other versions, distal end (182) may include self-righting features, as described above. Still further, in some versions distal end (182) may comprise a resilient material such that that needle (190) deforms the resilient material when compressed against by compression member (180). Optionally, compression member (180) may interface with proximal protrusions (168), such as through rails or tracks, to restrict compression member (180) to longitudinal movement relative to rotatable member (160). Proximal end (184) of compression member (180) of the present example comprises a curved face that interfaces with a complementary curved face on a distal end (142) of pushing member (140). Accordingly, it should be understood that rotatable member (160) and compression member (180), when in a closed position such as that shown in FIGS. 2B-2C, form a substantially curved interface such that puck assembly (150) may be rotated relative to pushing member (140) while pushing member (140) continues to longitudinally compress needle (190) against distal protrusion (162) via compression member (180).

Pushing member (140) is longitudinally actuatable relative to base (130). In some versions, operation of the trigger, such as trigger (22), may actuate pushing member (140). In other versions, grasping arm (110) may include a camming feature (not shown) that actuates pushing member (140) distally as grasping arm (110) is pivoted. Of course other actuation assemblies and/or features may be used to longitudinally actuate pushing member (140) relative to base (130), as will be apparent to one of ordinary skill in the art in view of the teachings herein. Pushing member (140) may be formed of metal (such as stainless steel), thermoplastic, and/or any other material or combination of materials as will be apparent to one of ordinary skill in the art. Of course other configurations for compression member (180) and/or pushing member (140) will be apparent to one of ordinary skill in the art in view of the teachings herein.

Referring back to FIG. 3, distal protrusion (162) of the present example includes a cable recess (164) with a control cable (198) disposed therein to wrap around a distal portion of distal protrusion (162). Cable recess (164) and control cable (198) may be fixedly coupled together or, in some versions, cable recess (164) and control cable (198) may simply frictionally interface. Accordingly, it should be understood that control cable (198) is operable to rotate puck assembly (150) relative to base (130) when one end of control cable (198) is advanced distally while the other end of control cable (198) is retracted proximally. In the present example, control cable (198) is coupled to a toggle (not shown), such as toggle (24) described above, such that the toggle is operable to rotate puck assembly (150). Of course it should be understood that other components or features may be utilized to control the rotation of puck assembly (150) relative to base (130). For example, push/pull cables and/or rods may be coupled to puck assembly (150), such as to proximal protrusions (168), to rotate puck assembly (150). Further still, as will be described below in reference to FIGS. 4 and 5, a rack and pinion assembly (220) and/or a ratchet assembly (270) may be used to control the rotation of puck assembly (150) relative to base (130). Of course still further configurations to control the rotation of puck assembly (150) will be apparent to one of ordinary skill in the art in view of the teachings herein.

Referring back to FIG. 2A, initially a user positions needle (190) within needle recess (166) when puck assembly (150) is in a first, open position. Pushing member (140) is then actuated distally relative to base (130) such that needle (190) is compressed between compression member (180) and distal protrusion (162) when puck assembly (150) reaches a closed position as shown in FIG. 2B. In some versions pushing member (140) is actuated by the user pulling a trigger, such as trigger (22). Optionally, grasping arm (110) may include a camming feature to cam pushing member (140) when the trigger rotates grasping arm (110). Of course pushing member (140) may be operable separately from grasping arm (110) and grasping arm (110) may be pivoted before, after, or while pushing member (140) is actuated. In still other versions, grasping arm (110) may be omitted entirely. As noted above, distal protrusion (162) and/or distal end (182) may include self-righting features to perpendicularly orient needle (190) relative to stationary arm (120), though these features are merely optional and may be omitted.

With needle (190) substantially secured via pushing member (140) actuating compression member (180) to clamp needle (190) against distal protrusion (162), the user may then rotate puck assembly (150) via control cable (198) to change the angular orientation of needle (190) relative to a longitudinal axis of stationary arm (120), by rotating needle (190) about an axis that is transverse to the longitudinal axis of stationary arm (120). It should be understood that pushing member (140) continues to clamp needle (190) with compression member (180) even while puck assembly (150) is rotated. By way of example only, as shown in FIG. 2C, the user may rotate needle (190) counterclockwise to the orientation shown. Of course it should be understood that the user may rotate needle (190) clockwise as well. Thus, the needle holder and needle driver (100) may be used to both securely grasp needle (190) as well as change the orientation of needle (190) relative to a longitudinal axis of stationary arm (120). Such a needle holder and needle driver (100) may also include self-righting features to maintain needle (190) in a vertically perpendicular orientation relative to stationary arm (120). Of course still other configurations and/or features may be incorporated into needle driver (100), including one or more of the features described in greater detail below, among other various possible configurations/features that may be incorporated into needle driver (100) as will be apparent to those of ordinary skill in the art in view of the teachings herein.

Figure 4:
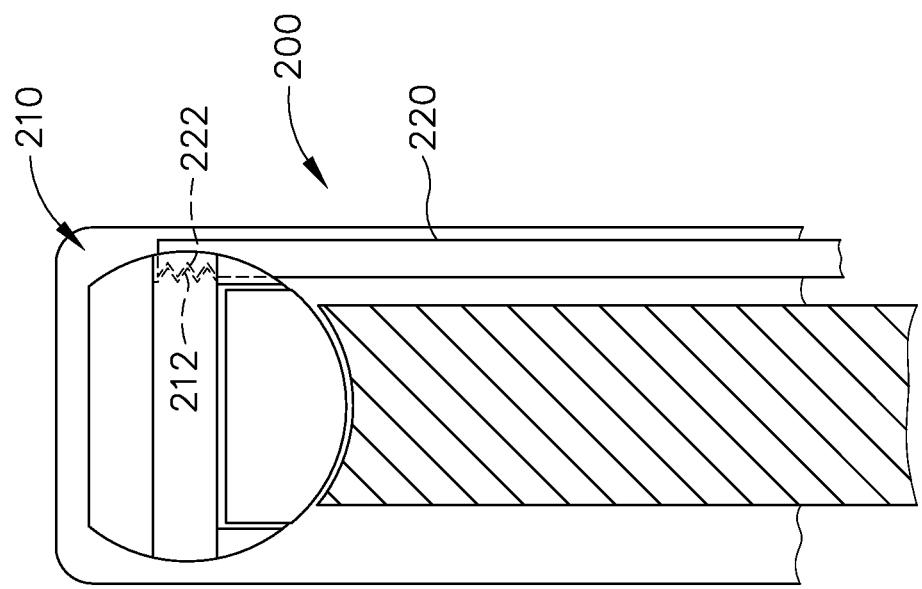
FIG. 4 depicts a top view of an exemplary needle driver with a grasping arm removed and showing a rack and pinion rotation assembly.

FIG. 4 depicts an exemplary alternative needle driver (200) for a needle holder having a rotatable puck assembly (210) and a rack member (220). Needle driver (200) and puck assembly (210) of the present example are constructed in substantial accordance with the teachings for needle driver (100) and puck assembly (150) described above. In addition, puck assembly (210) includes a plurality of teeth (212) (shown in phantom) circumferentially disposed about a bottom portion of puck assembly (210). Teeth (212) are configured to mesh with and engage one or more teeth (222) of a rack member (220), thereby forming a rack and pinion rotation assembly. Rack member (220) is coupled to a toggle (not shown), such as toggle (24), so that the toggle is operable to rotate puck assembly (210) when rack member (220) is longitudinally actuated. Thus, when rack member (220) is actuated distally relative to puck assembly (210), puck assembly (210) is rotated counterclockwise. Likewise, when rack member (220) is actuated proximally, puck assembly (210) is rotated clockwise. Of course puck assembly (210) and rack member (220) may have other configurations, as will be apparent to one of ordinary skill in the art in view of the teachings herein.

Figure 5:
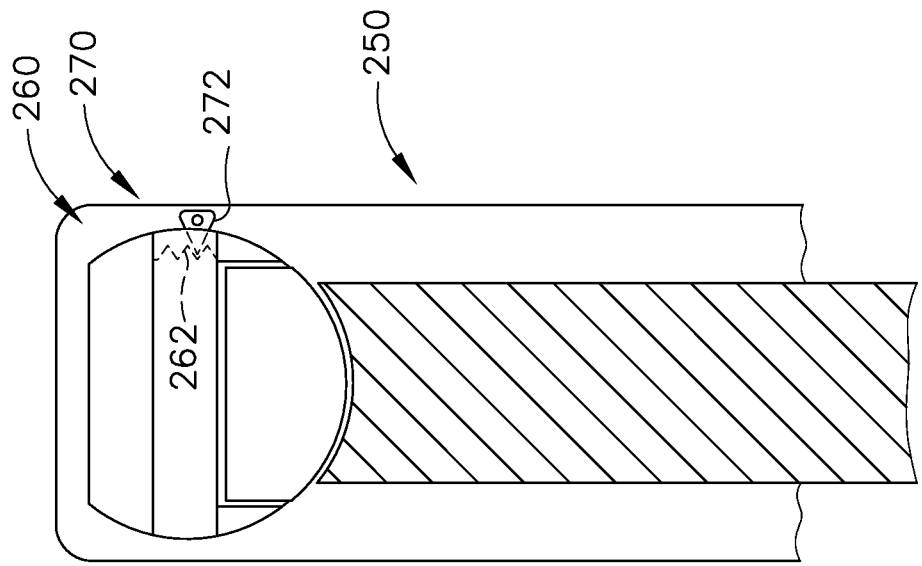
FIG. 5 depicts a top view of an exemplary needle driver with a grasping arm removed and showing a passive articulation assembly.

FIG. 5 depicts yet another alternative needle driver (250) for a needle holder having a rotatable puck assembly (260) and a ratchet assembly (270). Needle driver (250) and puck assembly (260) of the present example are constructed in substantial accordance with the teachings for needle driver (100) and puck assembly (150) described above. In addition, puck assembly (260) includes a plurality of teeth (262) circumferentially disposed about a bottom portion of puck assembly (260). Teeth (262) are configured to engage with a ratchet assembly (270). In the present example, ratchet assembly comprises a toothed member (272) acting as a pawl that engages teeth (262) to resist rotation of puck assembly (260). For example, in one version, toothed member (272) may comprise a resilient deformable member that deforms when sufficient force is applied and recovers its original shape when the next gap between teeth (262) is encountered. Accordingly, a user may push a needle, such as needle (190), against a surface (e.g., tissue, bone, another medical instrument, etc.) until toothed member (272) sufficiently deforms or deflects to ratchet to the next tooth (262). In another version, toothed member (272) may include one or more springs to bias toothed member (272) to resist rotation of puck assembly (260). In addition, or in the alternative, to the foregoing, a releasable lock (not shown) may be coupled to toothed member (272) such that a user may manually release ratchet assembly (270) to rotate puck assembly (260). By way of example only, a toggle, such as toggle (24), may be coupled to toothed member (272) (either directly or indirectly) to release ratchet assembly (270). Still other configurations for ratchet assembly (270) will be apparent to one of ordinary skill in the art in view of the teachings herein.

B. Exemplary Alternative Rotating Puck Articulation Assembly

Figure 6:
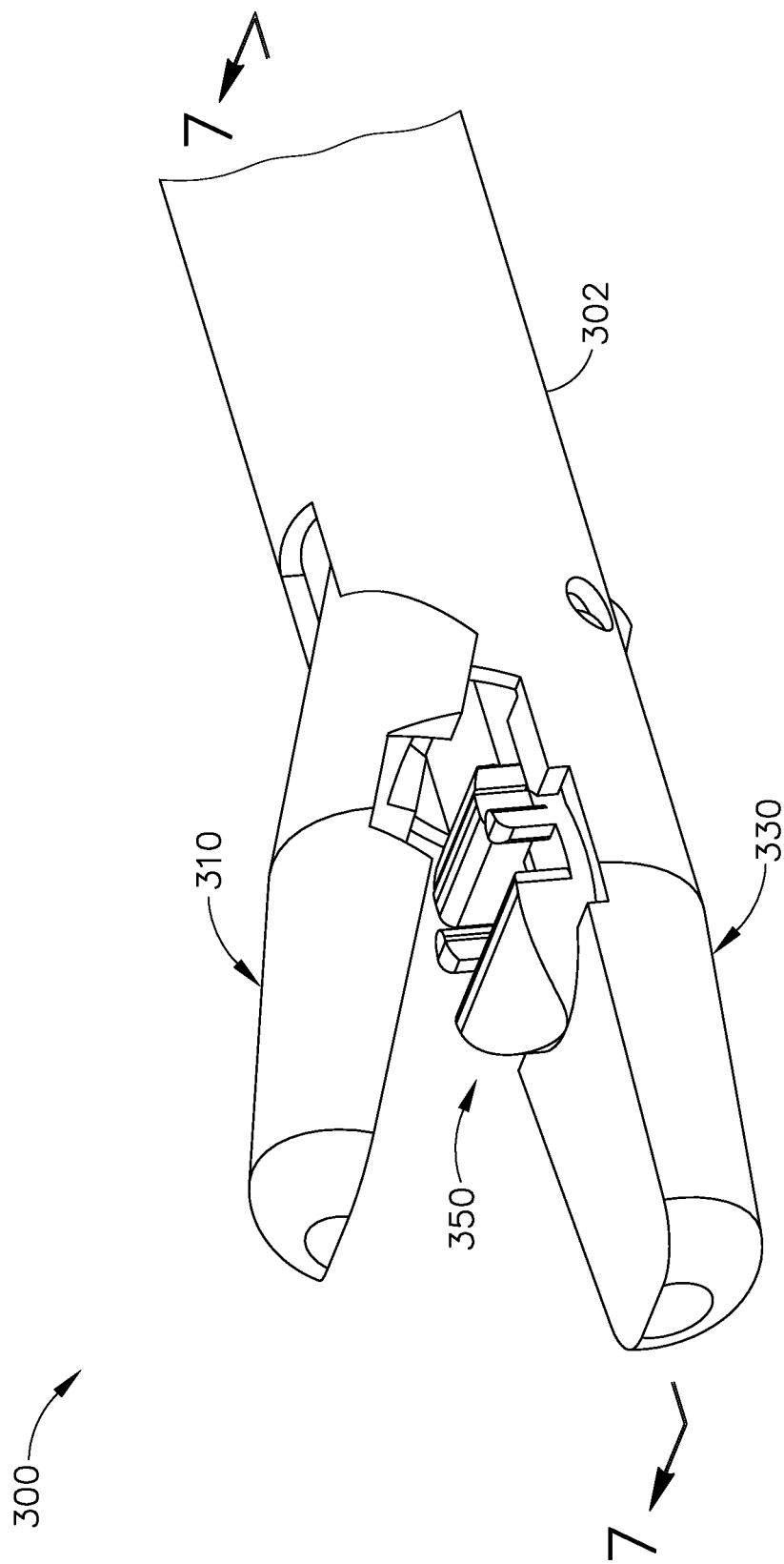
FIG. 6 depicts a perspective view of an exemplary alternative needle driver showing a rotating puck assembly having a self-righting assembly.
Figure 7A:
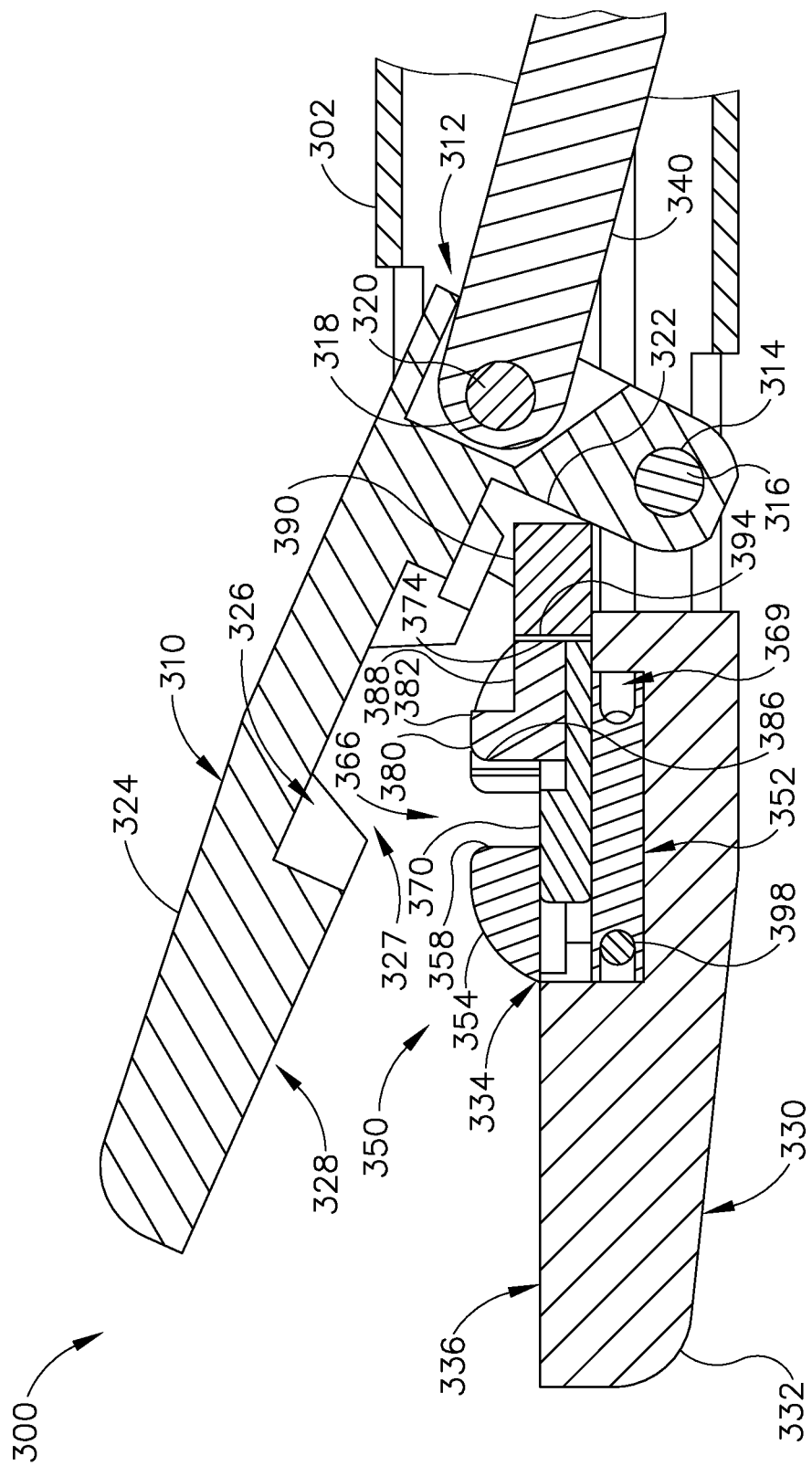
FIG. 7A depicts a side elevation cross-sectional view of the needle driver of FIG. 6 taken along section line 7-7 and shown in an open position.
Figure 7B:
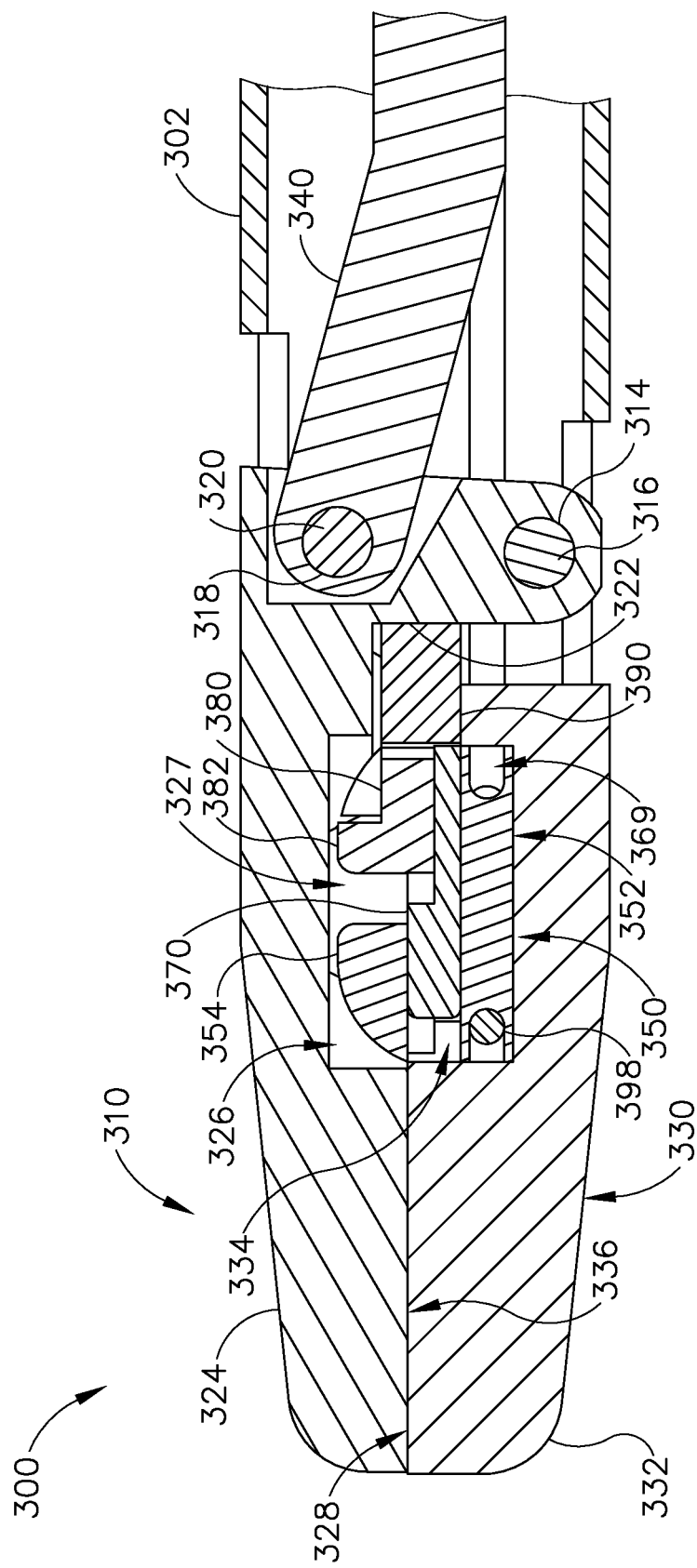
FIG. 7B depicts a side elevation cross-sectional view of the needle driver of FIG. 7A shown in a closed position.
Figure 8:
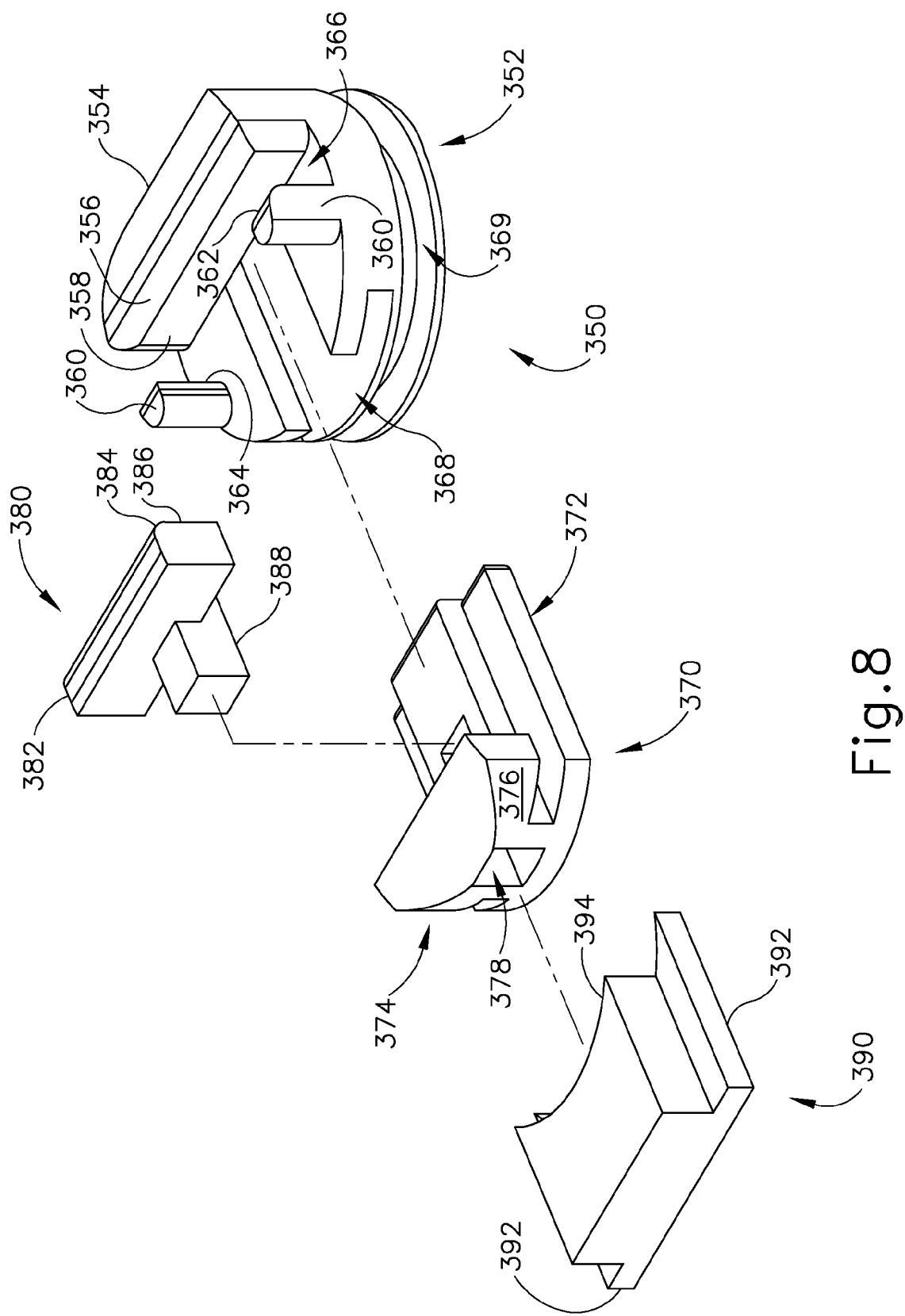
FIG. 8 depicts a rear exploded perspective view of the rotating puck assembly of FIG. 6.

FIGS. 6-8 depict yet another alternative needle driver (300) coupled to a distal end of a shaft (302) for a needle holder. Referring initially to FIG. 6, needle driver (300) comprises a grasping arm (310), a stationary arm (330), and an alternative rotating puck assembly (350). Grasping arm (310) is pivotable relative to stationary arm (330) via a trigger (not shown), such as trigger (22). In the present example, grasping arm (310) is pivotably coupled to shaft (302). In some versions, grasping arm may alternatively be pivotably coupled to stationary arm (330). Grasping arm (310) is operable to substantially vertically contain a needle (not shown), such as needle (190) between grasping arm (310) and stationary arm (330) such that a user may maneuver the needle with the needle holder. The needle may be constructed in accordance with at least some of the teachings of U.S. Pat. No. 6,056,771, entitled "Radiused Tip Surgical Needles and Surgical Incision Members," issued May 2, 2000; U.S. Pub. No. 2010/0100125, entitled "Suture Needle and Suture Assembly," published Apr. 22, 2010; U.S. Provisional Application Ser. No. 61/413,680, entitled "Custom Needle for Suture Instrument," filed Nov. 15, 2010; U.S. patent application Ser. No. 13/295,186, entitled "Needle for Laparoscopic Suturing Instrument," filed on Nov. 14, 2011, published as U.S. Pub. No. 2012/0123471 on May 17, 2012, the disclosures of which are incorporated by reference herein; and/or in any other manner as will be apparent to one of ordinary skill in the art in view of the teachings herein.

It should be understood that grasping arm (310) of the present example does not tightly grip the needle against stationary arm (330). Rather, puck assembly (350) longitudinally clamps the needle to substantially secure the needle relative to stationary arm (330), as will be described in greater detail below. Grasping arm (310) may be formed of metal (such as stainless steel), thermoplastic, and/or any other material or combination of materials as will be apparent to one of ordinary skill in the art. Referring to FIGS. 7A-7B, grasping arm (310) includes a pivot end (312) and a main body (324). Pivot end (312) includes a first pivot (314) and a second pivot (318). First pivot (314) is rotatably coupled to shaft (302) via a first pin (316). Second pivot (318) is offset from first pivot (314) and is rotatably coupled to an actuation member (340) via a second pin (320). Thus, when actuation member (340) is actuated longitudinally relative to shaft (302), first pin (316) and pivot (314) provide a mechanical ground about which grasping arm (310) pivots. In addition, a front portion of pivot end (312) includes a camming surface (322). Camming surface (322) is configured to engage and longitudinally actuate a pushing member (390) when grasping arm (310) is pivoted to a closed position, such as that shown in FIG. 7B, as will be described in greater detail below. Of course, it should be understood that, in some versions, grasping arm (310) may not engage pushing member (390). Instead, pushing member (390) may be actuated via a separate assembly, such as a toggle or slider. In such a configuration, grasping arm (310) may be pivoted to contain a needle between grasping arm (310) and stationary arm (330) prior to longitudinally clamping the needle with puck assembly (350).

Referring now to FIG. 7A, main body (324) of grasping arm (310) includes a recessed portion (326) and a front portion (328). Recessed portion (326) is sized to receive a top portion of puck assembly (350) therein while permitting puck assembly (350) and the needle to rotate within recessed portion (326). In the present example, side notches (327) are formed in sides of main body (324) at a longitudinal location where recessed portion (326) is located such that the needle is permitted to extend outwardly from main body (324) and rotate relative to main body (324). In addition, in some versions, notches (327) may assist in capturing needle and/or righting between grasping arm (310) and stationary arm (330), as will be described in greater detail below. Front portion (328) comprises an elongate surface extending distally from recessed portion (326). In the present example, front portion (328) is substantially flat, though this is merely optional. In some versions, front portion (328) may include ridging, divots, suture cutting features, frictional padding, and/or other features. For example, such ridging may assist in grasping and/or holding onto material (such as tissue, suture, a needle, etc.). In addition, or in the alternative, front portion (328) may include a self-righting needle feature such that front portion (328) may be used to grasp and right a needle without using puck assembly (350) and/or to grasp and right a needle from another needle holder. Of course main body (324) and/or grasping arm (310) may have other configurations, as will be apparent to one of ordinary skill in the art in view of the teachings herein.

Stationary arm (330) is fixedly coupled to shaft (302) and comprises a second main body (332) having a recessed portion (334) that receives rotating puck assembly (350) therein. Main body (332) further includes a pair of horizontally recessed longitudinal extending tracks (not shown) into which a pair of horizontal protrusions (392) (shown in FIG. 8) of pushing member (390) insert and travel along as pushing member (390) is actuated distally. Of course such tracks are merely optional and may be omitted. In addition, stationary arm (330) includes a front portion (336) extending distally from recessed portion (334). In the present example, front portion (336) is substantially flat, though this is merely optional. In some versions, front portion (336) may include ridging, divots, suture cutting features, frictional padding, and/or other features. For example, such ridging may assist in grasping and/or holding onto material (such as tissue, suture, a needle, etc.). In addition, or in the alternative, front portion (336) may include a self-righting needle feature such that front portion (336) (either in cooperation with a complementary feature on front portion (328) of grasping arm (310) or alone) may be used to grasp and right a needle without using puck assembly (350) and/or to grasp and right a needle from another needle holder. Of course main body (332) and/or stationary arm (330) may have other configurations, as will be apparent to one of ordinary skill in the art in view of the teachings herein.

Puck assembly (350) and pushing member (390) are shown in FIG. 8 in an exploded view. Pushing member (390) comprises an inverted T-shaped sled having a pair of horizontal protrusions (392) that each ride within a corresponding longitudinal track formed in stationary arm (330), though these are merely optional and may be omitted. Pushing member (390) also includes a distal end (394) having a curved surface. As will be described in greater detail below, distal end (394) is complementary to the curvature of a lower compression member (370) and a base member (352) of puck assembly (350). As will also be described in greater detail below, pushing member (390) is actuated distally via a camming surface (322) of grasping arm (310) such that pushing member (390) actuates lower compression member (370) and an upper compression member (380) relative to base member (352) of puck assembly (350) such that upper compression member (380) and base member (352) clamp onto a needle (not shown). Of course it should be understood that pushing member (390) may have other geometric configurations as well and/or may be omitted entirely.

Puck assembly (350) comprises base member (352), lower compression member (370), and upper compression member (380). Base member (352) comprises a substantially cylindrical member, though this is merely optional. In some versions, base member (352) may simply have a curved proximal end. The curvature of base member (352) and/or the curved proximal end is complementary to the curvature of distal end (394) of pushing member (390) such that base member (352) is able to rotate relative to pushing member (390) even when pushing member (390) abuts base member (352). Base member (352) further includes a distal protrusion (354), a pair of proximal protrusions (360), a needle recess (366) formed between distal protrusion (354) and proximal protrusions (360), and a compression member recess (368). Needle recess (366) is sized to receive at least a portion of a needle therein. In addition, base member (352) of the present example further includes a cable recess (369) formed in a lower portion of base member (352) that is configured to engage with a control cable (398) (shown in FIGS. 7A-7B). Similar to control cable (198) and cable recess (164) described above, control cable (398) and cable recess (369) are configured to rotate puck assembly (350) relative to stationary arm (330). In some versions, control cable (398) is physically coupled to cable recess (369) (e.g., via a pin, tack weld, or other anchoring device), while in other versions control cable (398) may merely frictionally engage with cable recess (369). Of course it should be understood that control rods, a rack and pinion assembly, or passive actuation assembly, such as those described above, can be used as well.

Distal protrusion (354) of the present example includes a cambered surface (356) and a flat surface (358). Cambered surface (356) may be configured to assist in guiding a needle into needle recess (366) while flat surface (358) may engage with flat portions of the needle to self-right the needle as it enters into needle recess (366) and/or is compressed against distal protrusion (354) by upper compression member (380), though this is merely optional and may be omitted. As one merely illustrative alternative, cambered surface (356) may comprise a chamfered surface or have any other suitable configuration. Of course distal protrusion (354) may be further constructed in accordance with at least some of the teachings of distal protrusion (162) described above and/or otherwise, as will be apparent to one of ordinary skill in the art in view of the teachings herein.

Proximal protrusions (360) also each include a cambered surface (362) and a flat surface (364). Cambered surface (362) may be configured to assist in guiding a needle into needle recess (366) while flat surface (364) may engage with flat portions of the needle to self-right the needle as it enters into needle recess (366) and/or is compressed against distal protrusion (354) by upper compression member (380), though this is merely optional and may be omitted. Again, cambered surfaces (362) may instead comprise chamfered surfaces or have any other suitable configuration. Of course proximal protrusions (360) may be further constructed in accordance with at least some of the teachings of proximal protrusions (168) described above and/or otherwise, as will be apparent to one of ordinary skill in the art in view of the teachings herein.

Still referring to FIG. 8, compression member recess (368) comprises an inverted T-shaped longitudinal recess configured to longitudinally receive a portion of an inverted T-shaped lower portion (372) of lower compression member (370). Accordingly, lower compression member (370) may be slid along compression member recess (368) relative to base member (352). Of course it should be understood that compression member recess (368) may have other geometric configurations as well and/or may be omitted.

Lower compression member (370) comprises an inverted T-shaped lower portion (372) and a proximal end portion (374). A longitudinal notch (378) is formed in a portion of lower portion (372) and extends proximally through proximal end portion (374). Longitudinal notch (378) is configured to receive a longitudinal portion (388) of upper compression member (380) therein. Proximal end portion (374) comprises a curved proximal face (376) that is complementary to the curvature of distal end (394) of pushing member (390). It should be understood that lower compression member (370) and base member (352) are able to rotate relative to pushing member (390) even when pushing member (390) abuts lower compression member (370) and base member (352).

Upper compression member (380) comprises a transverse clamp portion (382) and a longitudinal portion (388) extending perpendicular to transverse clamp portion (382). In the present example, transverse clamp portion (382) comprises a cambered surface (384) and a vertical flat distal surface (386). Cambered surface (384) may be configured to assist in guiding a needle into needle recess (366) while flat surface (386) may engage with flat portions of the needle to self-right the needle as it enters into needle recess (366) and/or is compressed against distal protrusion (354) by upper compression member (380), though this is merely optional and may be omitted. Again, cambered surface (384) may instead comprise a chamfered surface or have any other suitable configuration. Of course upper compression member (380) may be constructed otherwise, as will be apparent to one of ordinary skill in the art in view of the teachings herein.

Referring back to FIG. 7A, initially grasping arm (310) and puck assembly (350) are in the open position such that a needle may be manually inserted into needle recess (366) and/or the user may maneuver the needle holder into a position to pick up the needle. The user can then actuate the trigger to longitudinally actuate actuation member (340) to pivot grasping arm (310) about first pin (316) and first pivot (314) toward the closed position shown in FIG. 7B. As grasping arm (310) is pivoted toward stationary arm (330), camming surface (322) abuts and drives pushing member (390) distally. Distal end (394) of pushing member (390) engages with proximal end portion (374) of lower compression member (370) and a proximal end of longitudinal portion (388) of upper compression member (380) to simultaneously drive both distally. If the needle includes flat portions or other self-righting features, flat surface (386) of transverse clamp portion (382) and flat surface (358) of distal protrusion (354) may cooperatively compress against the needle and rotate the needle into a perpendicular orientation relative to stationary arm (330), substantially similar to the orientation of needle (190) shown in FIG. 3. With the needle clamped between distal protrusion (354) and transverse clamp portion (382), for example when needle driver (300) is in the closed position shown in FIG. 7B, the user may operate a toggle or other feature to engage control cable (398) to rotate puck assembly (350) relative to stationary arm (330). Accordingly, a user can rotate the needle to a desired angular orientation relative to a longitudinal axis of the needle holder, about an axis that is transverse to the longitudinal axis of the needle holder.

In some versions, grasping arm (310) may omit camming surface (322) and pushing member (390) may instead be independently actuated longitudinally via a toggle, slider, and/or other feature. Accordingly, the needle may initially be captured between grasping arm (310) and stationary arm (330) within needle recess (366) prior to pushing member (390) clamping the needle between upper compression member (380) and distal protrusion (354). Of course still other configurations and/or operations will be apparent to one of ordinary skill in the art in view of the teachings herein. In addition, or in the alternative, the needle may include additional flat portions at a distal end such that a user can consistently grasp and maintain the needle in substantially the same orientation.

C. Exemplary Combination Rotating Puck Articulation Assembly

Figure 9:
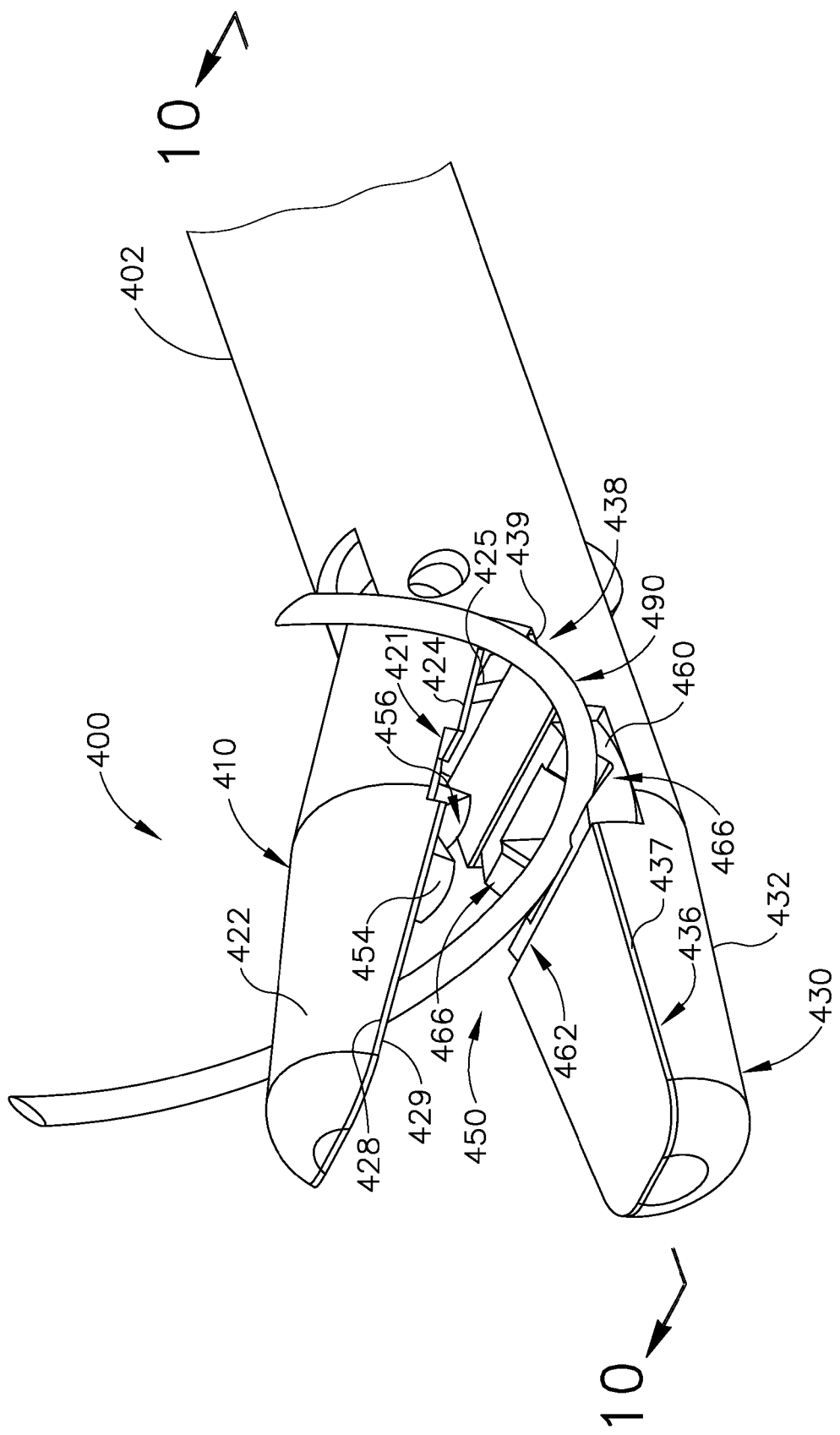
FIG. 9 depicts a perspective view of another exemplary alternative needle driver showing a rotating puck assembly with an alternative self-righting assembly.
Figure 10A:
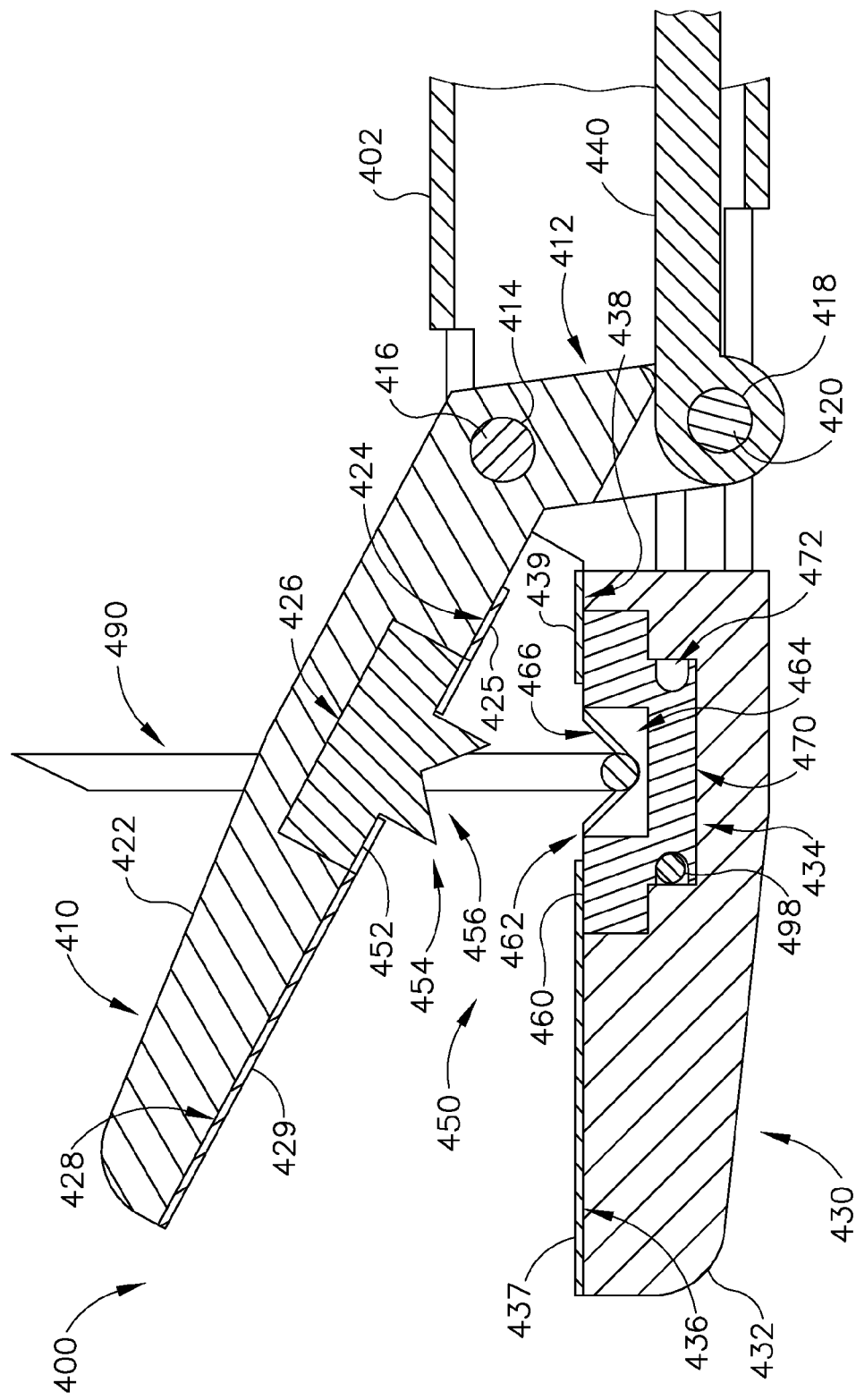
FIG. 10A depicts a side elevation cross-sectional view of the needle driver of FIG. 9 taken along section line 10-10 and shown in an open position.
Figure 10B:
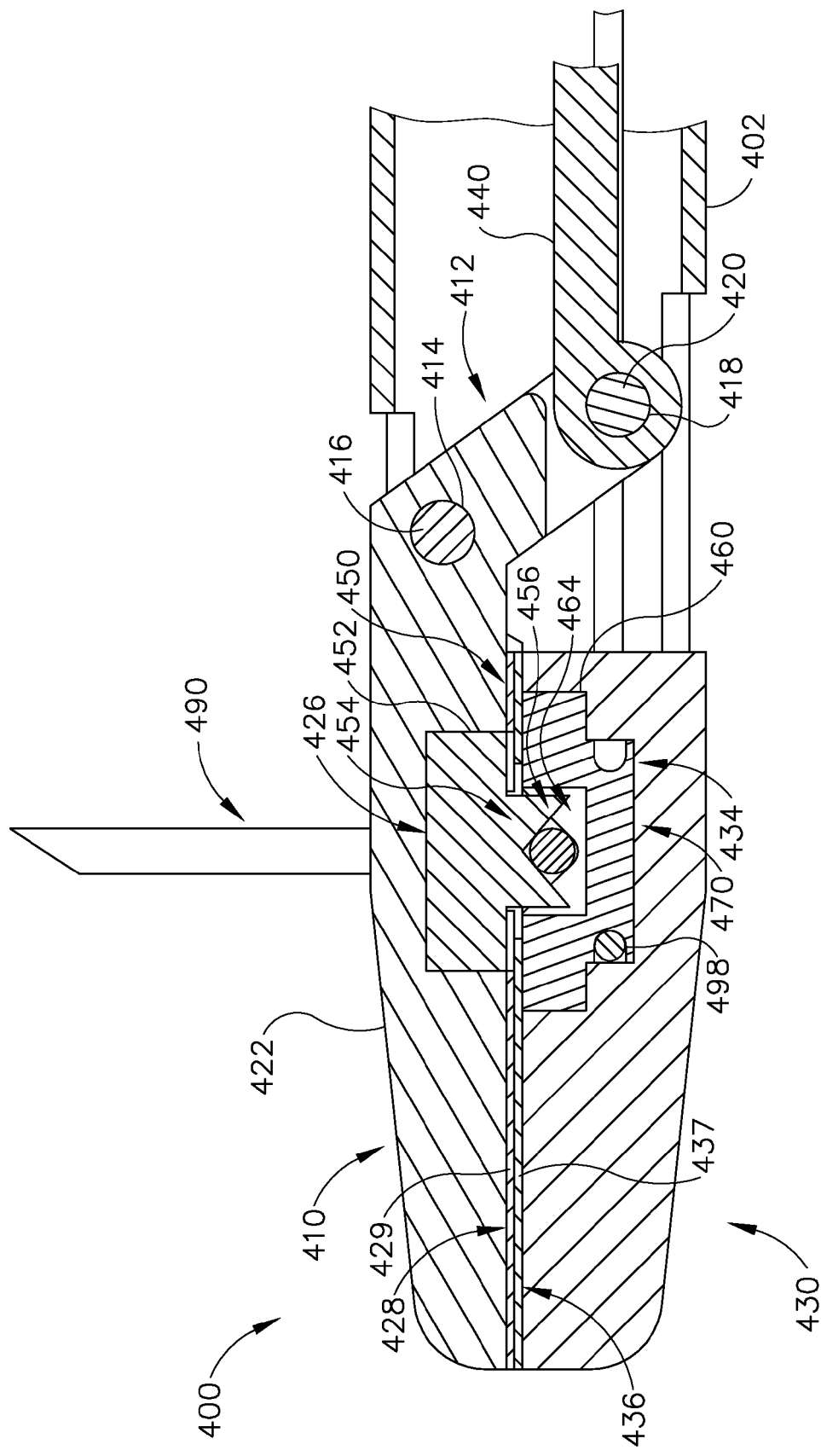
FIG. 10B depicts a side elevation cross-sectional view of the needle driver of FIG. 10A shown in a closed position.
Figure 10C:
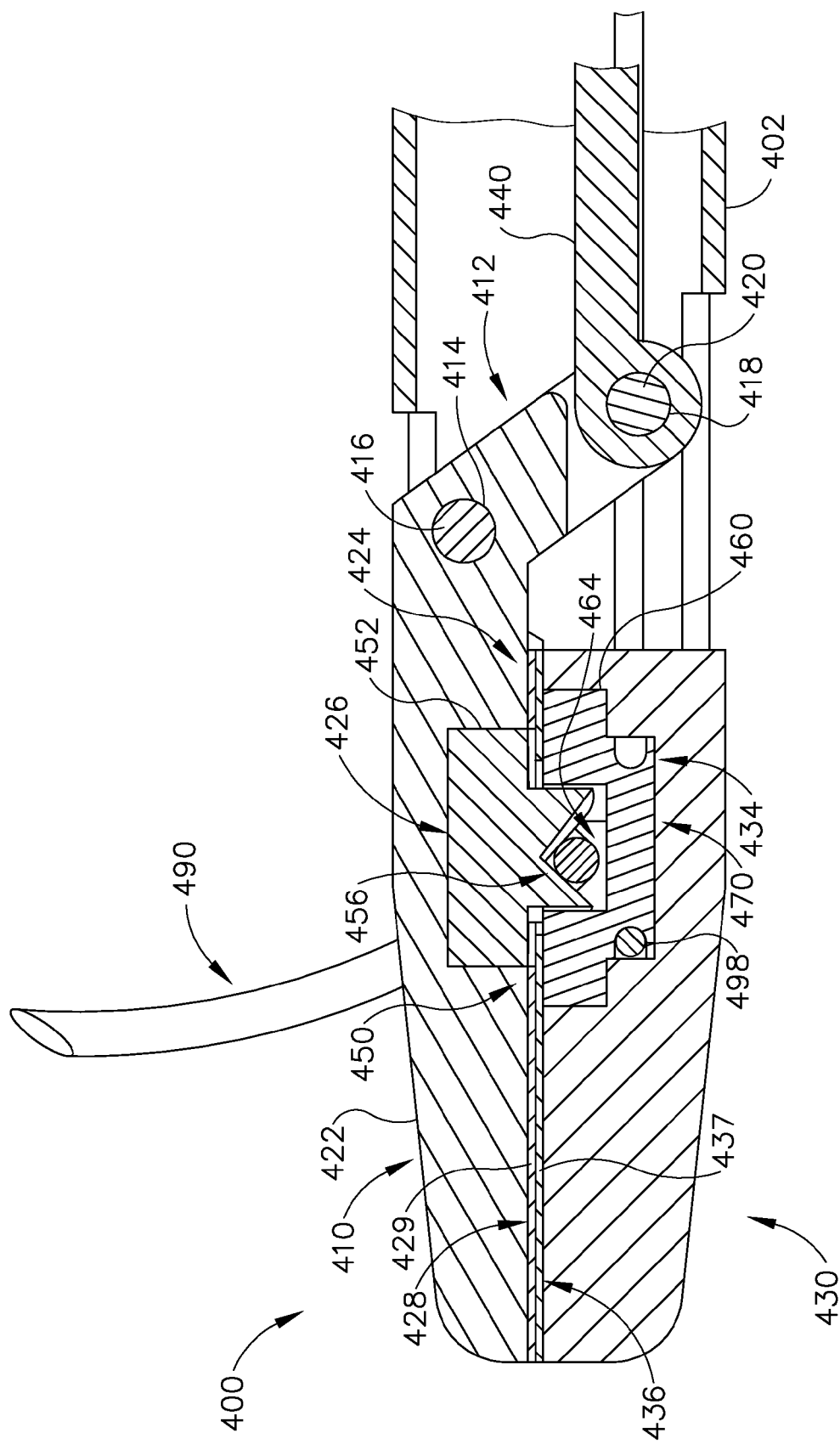
FIG. 10C depicts a side elevation cross-sectional view of the needle driver of FIG. 10A shown in a rotated position.

FIGS. 9-10C depict still another alternative needle driver (400) coupled to a distal end of a shaft (402) for a needle holder. Referring initially to FIG. 9, needle driver (400) comprises a grasping arm (410), a stationary arm (430), and a two-piece rotating puck assembly (450) to grasp and rotate a needle (490). Needle (490) may include one or more self-righting features, such as opposing flat surfaces, notches, ovular portions, non-circular portions, etc., though these are merely optional. In addition, such features may be located at a mid-point of needle (490), at an end, and/or at any other location on needle (490). In some versions, one or more features of puck assembly (450) cooperate with the curvature of needle (490) and/or with one or more self-righting features of needle (490) such that needle (490) contacts puck assembly (450) at three or more different points to provide self-righting of needle (490) as needle (490) is grasped by puck assembly (450). Needle (490) may be further constructed in accordance with at least some of the teachings of U.S. Pat. No. 6,056,771, entitled "Radiused Tip Surgical Needles and Surgical Incision Members," issued May 2, 2000; U.S. Pub. No. 2010/0100125, entitled "Suture Needle and Suture Assembly," published Apr. 22, 2010; U.S. Provisional Application Ser. No. 61/413,680, entitled "Custom Needle for Suture Instrument," filed Nov. 15, 2010; U.S. patent application Ser. No. 13/295,186, entitled "Needle for Laparoscopic Suturing Instrument," filed on Nov. 14, 2011, published as U.S. Pub. No. 2012/0123471 on May 17, 2012, the disclosures of which are incorporated by reference herein; and/or in any other manner as will be apparent to one of ordinary skill in the art in view of the teachings herein.

Grasping arm (410) is pivotable relative to stationary arm (430) via a trigger (not shown), such as trigger (22). In the present example, grasping arm (410) is pivotably coupled to shaft (402). In some versions, grasping arm may alternatively be pivotably coupled to stationary arm (430). Grasping arm (410) clamps needle (490) between grasping arm (410) and stationary arm (430) such that a user may maneuver needle (490) with the needle holder. Grasping arm (410) may be formed of metal (such as stainless steel), thermoplastic, and/or any other material or combination of materials as will be apparent to one of ordinary skill in the art. Referring to FIGS. 10A-10C, grasping arm (410) includes a pivot end (412) and a main body (422). Pivot end (412) includes a first pivot (414) and a second pivot (418). First pivot (414) is rotatably coupled to shaft (402) via a first pin (416). Second pivot (418) is offset from first pivot (414) and is rotatably coupled to an actuation member (440) via a second pin (420). Thus, when actuation member (440) is actuated longitudinally relative to shaft (402), first pin (416) and pivot (414) provide a mechanical ground about which grasping arm (410) pivots.

Referring now to FIG. 10A, main body (422) of grasping arm (410) includes a recessed portion (426), a front portion (428), and a rear portion (424). Recessed portion (426) is sized to receive a top member (452) of puck assembly (450) therein, as will be described in greater detail below. In the present example, side notches (421) (shown in FIG. 9) are formed in sides of main body (422) at a longitudinal location such that needle (490) is permitted to extend outwardly from main body (422) and rotate relative to main body (422). In addition, in some versions, notches (421) may assist in capturing needle (490) between grasping arm (410) and stationary arm (430), as will be described in greater detail below. Front portion (428) comprises an elongate surface extending distally from recessed portion (426). Rear portion (424) comprises a surface extending proximally from recessed portion (426).

In the present example, front portion (428) and rear portion (424) are substantially flat and include a front cover plate (429) and a rear cover plate (425), respectively, though these are merely optional and may be omitted. Cover plates (425, 429) are configured to retain top member (452) of puck assembly (450) within recessed portion (426) of grasping arm (410). In some versions, grasping arm (410) may be formed about top member (452) during manufacture such that cover plates (425, 429) may be omitted. In some versions, front portion (428) and/or front cover plate (429) may include ridging, divots, suture cutting features, frictional padding, and/or other features. For example, such ridging may assist in grasping and/or holding onto material (such as tissue, suture, needle (490), etc.). In addition, or in the alternative, front portion (428) and/or front cover plate (429) may include a self-righting needle feature such that front portion (428) and/or front cover plate (429) may be used to grasp and right needle (490) without using puck assembly (450) and/or to grasp and right needle (490) held by another needle holder. In some versions, rear cover plate (425) may incorporate any of the foregoing features and may have a different feature than front cover plate (429) (e.g., rear cover plate (425) may include a suture severing feature while front cover plate (429) includes ridging). Of course main body (424) and/or grasping arm (410) may have other configurations, as will be apparent to one of ordinary skill in the art in view of the teachings herein.

Stationary arm (430) is fixedly coupled to shaft (402) and comprises a second main body (432) having a recessed portion (434) that receives a bottom member (460) of puck assembly (450) therein. In addition, stationary arm (430) includes a front portion (436) extending distally from recessed portion (434) and a rear portion (438) proximal of recessed portion (434). In the present example, front portion (436) and rear portion (438) are substantially flat and include a front cover plate (437) and rear cover plate (439), though these are merely optional and may be omitted. Front cover plate (437) and rear cover plate (439) extend over a portion of bottom member (460) and are configured to substantially retain bottom member (460) within recessed portion (434). In some versions, front portion (436) and/or front cover plate (437) may include ridging, divots, suture cutting features, frictional padding, and/or other features. For example, such ridging may assist in grasping and/or holding onto material (such as tissue, suture, needle (490), etc.). In addition, or in the alternative, front portion (436) and/or front cover plate (437) may include a self-righting needle feature such that front portion (436) and/or front cover plate (437) (either in cooperation with a complementary feature on front portion (428) and/or cover plate (429) of grasping arm (410) or alone) may be used to grasp and right needle (490) without using puck assembly (450) and/or to grasp and right needle (490) grasped by another needle holder. In some versions, rear cover plate (439) may incorporate any of the foregoing features and may have a different feature than front cover plate (437) (e.g., rear cover plate (439) may include a suture severing feature while front cover plate (437) includes ridging). Of course main body (432) and/or stationary arm (430) may have other configurations, as will be apparent to one of ordinary skill in the art in view of the teachings herein.

Puck assembly (450) comprises a top member (452) and a bottom member (460). Top member (452) comprises a substantially cylindrical member having a needle-righting feature (454). In the example shown in FIGS. 9-10C, needle-righting feature (454) comprises a protrusion having an angular recess (456). As will be discussed in greater detail below, angular recess (456) is configured to engage with needle (490) to orient needle (490) perpendicularly to stationary arm (430) when grasping arm (410) is pivoted to the closed position, as shown in FIG. 10B. Of course it should be understood that other needle-righting features may be incorporated into top member (452) either in addition, or in the alternative, to needle-righting feature (454).

Bottom member (460) also comprises a substantially cylindrical member. In the present example, bottom member (460) comprises a needle capture portion (462) and a control portion (470). Needle capture portion (462), shown best in FIG. 9, includes a central recess (464) and a pair of angular recesses (466) disposed on either side of central recess (464). Central recess (464) comprises a cuboid recess having a substantially flat base that is parallel to the top of stationary arm (430). In addition, central recess (464) is configured to receive needle-righting feature (454) therein, thereby substantially rotatably coupling together top member (452) and bottom member (460) when grasping arm (410) is pivoted to the closed position shown in FIG. 10B. Angular recesses (466) comprise substantially right angled recesses that form a V-shape relative to central recess (464). Thus, angular recesses (466) engage with needle (490) to right needle (490) when grasping arm (410) is pivoted to the closed position. Of course it should be understood that needle capture portion (462) may have other configurations for grasping and/or righting needle (490) when grasping arm (410) is pivoted to the closed position.

Control portion (470) of bottom member (460) includes a cable recess (472) that is configured to engage with a control cable (498) (shown in FIGS. 10A-10C). Similar to control cable (198) and cable recess (164) described above, control cable (498) and cable recess (472) are configured to rotate bottom member (460) relative to stationary arm (430). In some versions, control cable (498) is physically coupled to cable recess (472) (e.g., via a pin, tack weld, or other anchoring device), while in other versions control cable (498) may merely frictionally engage with cable recess (472). Of course it should be understood that control rods, a rack and pinion assembly, or passive actuation assembly, such as those described above, can be used as well.

Referring back to FIG. 10A, initially grasping arm (410) and puck assembly (450) are in the open position such that needle (490) may be manually inserted into needle capture portion (462) and/or the user may maneuver the needle holder into a position to pick up needle (490). The user then actuates the trigger to longitudinally actuate actuation member (440) to pivot grasping arm (410) about first pin (416) and first pivot (414) toward the closed position shown in FIG. 10B. As grasping arm (410) is pivoted toward stationary arm (430), angular recess (456) of top member (452) engages needle (490) as arms (410, 430) are clamped together to right needle (490). It should be understood that angular recess (456) of top member (452) and angular recesses (466) of bottom member (460) form a three-point contact assembly that rights needle (490) due to the curvature of needle (490). Once arms (410, 430) are clamped together, as shown in FIG. 10B, the user may operate a toggle or other feature to engage control cable (498) to rotate puck assembly (450) relative to grasping arm (410) and stationary arm (430). Accordingly, a user can rotate needle (490) to a desired angular orientation relative to a longitudinal axis of the needle holder, such as that shown in FIG. 10C. In the present example, top member (452) passively rotates within recessed portion (426) of grasping arm (410) while bottom member (460) is rotated via control cable (498), though this is merely optional. In some versions, top member (452) may be rotated by control cable (498) and/or both top member (452) and bottom member (460) may be rotated by control cables. Of course other configurations and/or operations for needle driver (400) and/or puck assembly (450) will be apparent to one of ordinary skill in the art in view of the teachings herein.

D. Exemplary Rotating Collet Articulation Assembly

Figure 11:
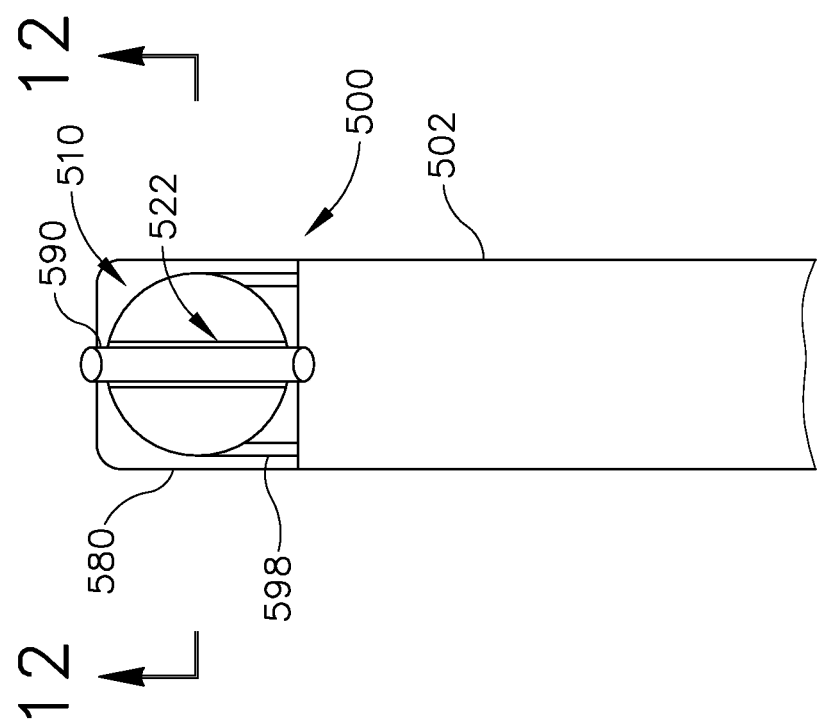
FIG. 11 depicts a top view of yet another exemplary needle driver showing an exemplary turntable.
Figure 12:
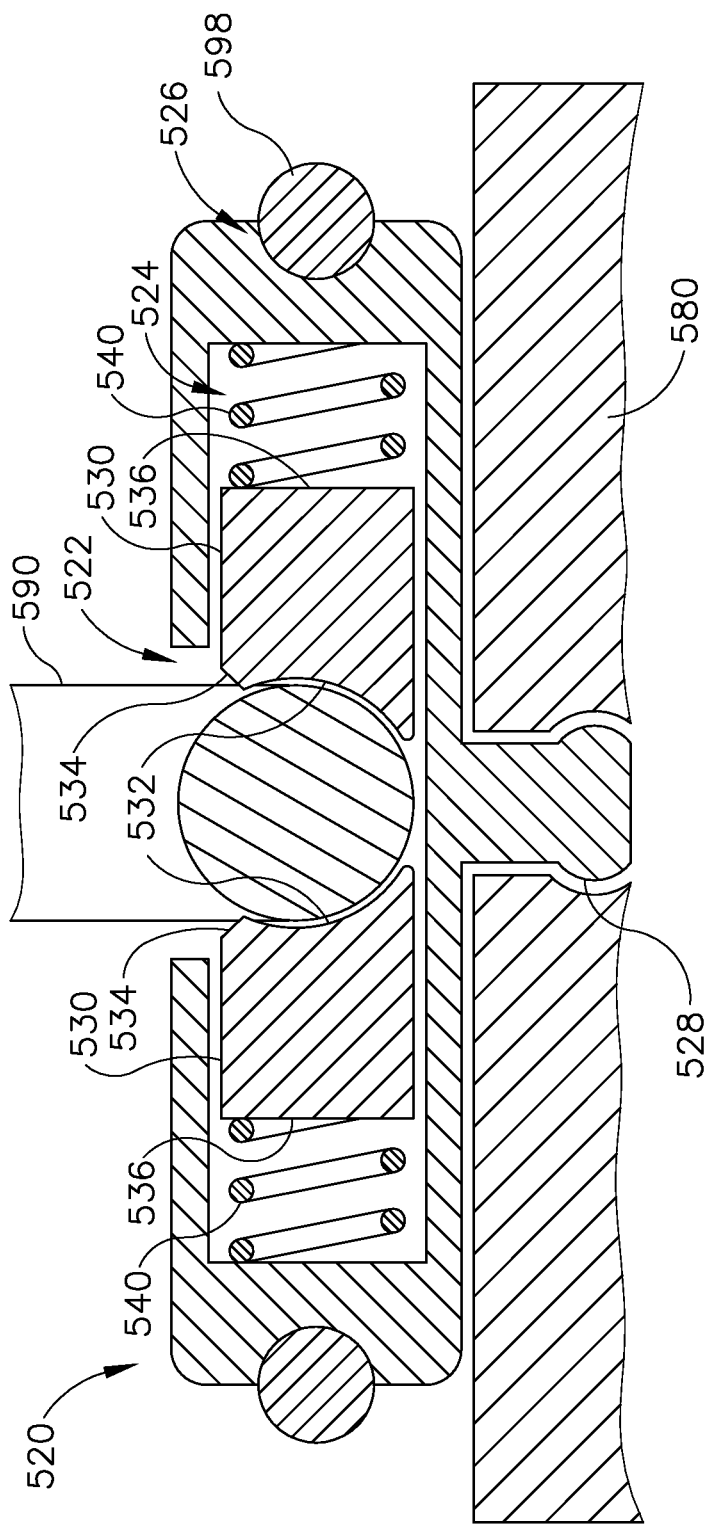
FIG. 12 depicts a side elevation cross-sectional view of the needle driver of FIG. 11 taken along section line 12-12 and showing a pair of spring-loaded collets.

FIGS. 11-12 depict yet another exemplary needle driver (500) coupled to a distal end of a shaft (502) for a needle holder. As shown in FIG. 11, needle driver (500) comprises a stationary arm (580) having a rotating collet assembly (510) pivotably mounted thereon with an exemplary needle (590) inserted into a needle recess (522) of collet assembly (510). In some versions, a grasping arm (not shown) may be pivotably coupled to shaft (502) and/or stationary arm (580) to clamp or otherwise hold needle (590) against stationary arm (580), though this is merely optional. Needle (590) may be constructed in accordance with at least some of the teachings of U.S. Pat. No. 6,056,771, entitled "Radiused Tip Surgical Needles and Surgical Incision Members," issued May 2, 2000; U.S. Pub. No. 2010/0100125, entitled "Suture Needle and Suture Assembly," published Apr. 22, 2010; U.S. Provisional Application Ser. No. 61/413,680, entitled "Custom Needle for Suture Instrument," filed Nov. 15, 2010; U.S. patent application Ser. No. 13/295,186, entitled "Needle for Laparoscopic Suturing Instrument," filed on Nov. 14, 2011, published as U.S. Pub. No. 2012/0123471 on May 17, 2012, the disclosures of which are incorporated by reference herein; and/or in any other manner as will be apparent to one of ordinary skill in the art in view of the teachings herein.

FIG. 12 shows an enlarged cross-sectional view of collet assembly (510) having a turntable (520), a control cable (598), and a pair of locking collets (530). In the present example, turntable (520) comprises a cylindrical member having a needle recess (522), an interior channel (524), a cable recess (526) formed on an outer circumference of turntable (520), and a pivot pin (528). Pivot pin (528) comprises a cylindrical rod having a bulbous end that is inserted into to stationary arm (580) such that turntable (520) is pivotable relative to stationary arm (580), but substantially vertically secured thereto. Needle recess (522) is sized and configured to receive a portion of needle (590) therein, such as a midpoint section of needle (590). Interior channel (524) comprises a horizontal channel formed inside of turntable (520) that is sized to contain a pair of collets (530) and springs (540) therein. In the present example, interior channel (524) comprises a cuboid channel, though this is merely optional. In some versions a cylindrical channel or any other geometrically shaped channel may be implemented. Cable recess (526) comprises a U-shaped channel formed in the circumference of turntable (520) that is configured to engage with control cable (598). Similar to control cable (198) and cable recess (164) described above, control cable (598) and cable recess (526) are configured to rotate turntable (520) relative to stationary arm (580). In some versions, control cable (598) is physically coupled to cable recess (526) (e.g., via a pin, tack weld, or other anchoring device), while in other versions control cable (598) may merely frictionally engage with cable recess (526). Of course it should be understood that control rods, a rack and pinion assembly, or passive actuation assembly, such as those described above, may be used as well.

Within interior channel (524) are a pair of opposing collets (530) and a pair of springs (540). Each collet (530) comprises a first end (532) and a second end (536) engaged with a corresponding spring (540). Springs (540) bias collets (530) toward each other to provide a clamping force when needle (590) is inserted into needle recess (522). In the present example, first ends (532) comprise a curved surface configured to substantially engage a curved portion of needle (590). Of course such curved surfaces are merely exemplary and other geometries and/or features may be incorporated into first ends (532) to engage with needle (590) (e.g., ledges, insertable pins, etc.). As shown in FIG. 12, each first end (532) also includes a chamfered edge (534) such that needle (590) can cam each collet (530) outwardly when needle (590) is initially inserted. Of course still further constructions and/or configurations for turntable (520) and/or collets (530) will be apparent to one of ordinary skill in the art in view of the teachings herein.

To use needle driver (500), initially a user inserts needle (590) and the needle holder inside a patient with suture coupled to needle (590). The user then inserts a portion of needle (590) into needle recess (522) of turntable (520). Needle (590) engages chamfered edges (534) to cam collets (530) apart until needle (590) inserts between collets (530). Springs (540) bias collets (530) against needle (590) to clamp needle (590) therein. With needle (590) secured within needle recess (520), the user can use a toggle or other feature coupled to control cable (598) to rotate turntable (520) and needle (590) relative to stationary arm (580). Thus, the user can adjust the orientation angle of needle (590) relative to a longitudinal axis of the needle holder. To remove needle (590) from turntable (520), the user pulls upon needle (590) to overcome springs (540) and urge collets (530) outwardly until needle (590) is clear of collets (530).

E. Exemplary Two Arm Articulation Assembly

FIGS. 13A-13B depict another exemplary needle driver (600) having a pair of longitudinally actuatable arms (610, 620) and a curved bearing surface (650). In the present example, needle driver (600) comprises a main body (602) having a distal end (604) that includes curved bearing surface (650). Curved bearing surface (650) comprises a substantially parabolic or otherwise curved surface against which a needle (690) may be rotated against, as will be described in greater detail below. Main body (602) further includes a pair of longitudinal channels (606) (shown in phantom) through which actuatable arms (610, 620) each extend. Channels (606) each terminate with a ledge (608) against which a corresponding spring (640) (shown in phantom) abuts and/or is coupled thereto, as will be described in greater detail below.

Actuatable arms (610, 620) are positioned on opposing sides of main body (602) and extend distally from distal end (604). In the present example, each actuatable arm (610, 620) includes a longitudinal shaft (612, 622), a terminating end (614, 624), and a proximal spring engaging portion (618, 628). Longitudinal shafts (612, 622) are coupled at a proximal end (not shown) to a toggle or other feature operable to longitudinally actuate arms (610, 620). Terminating ends (614, 624) comprise protrusions from longitudinal shafts (612, 622) that are configured to engage with needle (690). In the present example, terminating ends (614, 624) comprise rectangular protrusions that simply abut needle (690), though this is merely exemplary. In some versions, terminating ends (614, 624) may comprise curved surfaces, angled surfaces, etc. In addition, other features to engage with and/or secure needle (690) relative to arms (610, 620) may be included on terminating ends (614, 624), such as snaps, clamps, clips, etc. Furthermore, in some versions, terminating ends (614, 624) may be pivotably coupled to longitudinal shafts (612, 622) such that terminating ends pivot about needle (690) as needle (690) is rotated about bearing surface (650), as will be described below. Of course still further configurations for terminating ends (614, 624) will be apparent to one of ordinary skill in the art in view of the teachings herein.

As shown in FIG. 13A, spring engaging portions (618, 628) are each positioned distally of springs (640) such that each spring (640) is retained about its corresponding longitudinal shaft (612, 622) between spring engaging portion (618, 628) and ledge (608). In the present example, spring engaging portions (618, 628) are coupled to springs (640) such that longitudinal actuation of arms (610, 620) compresses or stretches springs (640), thereby biasing arms (610, 620) back to a neutral position, though this is merely optional.

As shown in FIG. 13A, initially a user inserts needle (690) between arms (610, 620) and bearing surface (650). In some versions, the user may initially translate arms (610, 620) distally, thereby stretching springs (640), to insert needle (690) between arms (610, 620) and bearing surface (650). Such biasing from springs (640) may substantially longitudinally clamp needle (690) against distal end (604) of main body (602). With needle (690) between arms (610, 620) and bearing surface (650), the user operates the toggle or other feature to longitudinally actuate arms (610, 620) relative to main body (602). In some versions, the toggle or other feature may simultaneously actuate a first arm (610) proximally while extending a second arm (620) distally. Of course arms (610, 620) may also be separately actuatable as well. When first arm (610) is actuated proximally and second arm (620) is actuated distally, needle (690) is pivoted about bearing surface (650) to change the angle of needle (690) relative to a longitudinal axis of the needle holder, such as that shown in FIG. 13B. Thus, the user may adjust the angle of needle (690) to a desired position during usage. In the present example, springs (640) bias arms (610, 620) back to a first position shown in FIG. 13A, though this is merely optional.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK® bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body portion;
   (b) a shaft coupled to the body portion and extending distally from the body portion, the shaft having a distal end and defining a longitudinal axis; and
   (c) a needle driver coupled to the distal end of the shaft, wherein the needle driver comprises:

(i) a first arm, (ii) a second arm, wherein the second arm is movable relative to the first arm between an open position and a closed position to selectively grasp a needle, (iii) a rotatable assembly, wherein the rotatable assembly comprises a first member and a second member configured to selectively engage with a needle, wherein the rotatable assembly is operable to rotate relative to the first arm and the second arm while selectively engaged with the needle to form a non-perpendicular angle relative to the longitudinal axis of the shaft, wherein the first member is disengaged from the second member when the second arm is in the open position, (iv) a first driving member, wherein the first driving member is configured to move longitudinally within the first arm to thereby cause the first member and the second member to engage the needle, wherein the first driving member and the second member of the rotatable assembly include complementary curved portions that enable the second member to rotate when the first driving member is advanced longitudinally to cause the first member and the second member to engage the needle; and (v) a second driving member, wherein the second driving member is configured to move longitudinally within the first arm to thereby cause rotation of the first member.

2. The apparatus of claim 1 wherein the body portion comprises a toggle, wherein the toggle is operable to rotate the rotatable assembly relative to the first arm.

3. The apparatus of claim 2 wherein the second driving member comprises a control cable, wherein the toggle is coupled to the control cable, wherein the control cable is operable to rotate the rotatable assembly.

4. The apparatus of claim 1 wherein the rotatable assembly comprises a self-righting feature.

5. The apparatus of claim 1 wherein the second arm is pivotable relative to the first arm from the open position to the closed position.

6. The apparatus of claim 5 wherein the first member is rotatably coupled to the first arm, wherein the second member is rotatably coupled to the second arm.

7. The apparatus of claim 6 wherein the first member engages with the second member when the second arm is pivoted to the closed position, wherein rotation of the first member rotates the second member.

8. The apparatus of claim 6 wherein the rotatable assembly is operable to self-right the needle when the second arm is pivoted to the closed position.

9. The apparatus of claim 6 wherein the first member is coupled to a toggle, wherein the toggle is operable to rotate the first member.

10. A needle holder comprising:

(a) a shaft having a distal end and defining a longitudinal axis, wherein the shaft includes a driving feature passing through an interior region of the shaft;

(b) a first arm coupled to the distal end of the shaft;

(c) a second arm pivotably coupled to the distal end of the shaft, wherein the second arm is pivotable from a first position to a second position; and (d) a rotatable puck assembly associated with the first arm and the second arm, wherein the rotatable puck assembly comprises a first rotatable member and a second rotatable member, wherein the rotatable puck assembly is configured to clamp about a portion of a needle, wherein the driving feature is translatable within the interior region of the shaft to thereby drive rotation of the first rotatable member, wherein the first member is configured to disengage the second member when the second arm is in the first position, wherein the first rotatable member is configured to engage the second rotatable member when the second arm is in the second position such that rotation of the first rotatable member causes concurrent rotation of the second member, and wherein the rotatable puck assembly is operable to rotate the needle relative to the first arm such that the needle forms a non-perpendicular angle to the longitudinal axis.

11. The needle holder of claim 10 wherein the second arm is operable to engage the rotatable puck assembly to clamp about the portion of the needle when the second arm is pivoted from the first position to the second position.

12. The needle holder of claim 10 wherein the rotatable puck assembly is operable to self-right the needle when the rotatable puck assembly clamps about the portion of the needle.

13. An apparatus comprising:

(a) a body portion;

(b) a shaft coupled to the body portion and extending distally from the body portion, the shaft having a distal end and defining a longitudinal axis; and (c) a needle driver coupled to the distal end of the shaft, wherein the needle driver comprises:

(i) a first arm, (ii) a second arm, wherein the second arm is movable relative to the first arm between an open position and a closed position to selectively grasp a needle, (iii) a rotatable assembly, wherein the rotatable assembly comprises a first member and a second member configured to selectively engage with a needle, wherein the rotatable assembly is operable to rotate relative to rotate the needle relative to the first and second arms, wherein the first member is disengaged from the second member when the second arm is in the open position, (iv) a first driving member, wherein the first driving member is configured to move longitudinally within the first arm to thereby cause the first member and the second member to engage the needle, wherein the first driving member and the second member of the rotatable assembly include complementary curved portions that enable the second member to rotate when the first driving member is advanced longitudinally to cause the first member and the second member to engage the needle, and (v) a second driving member, wherein the second driving member is configured to move longitudinally within the first arm to thereby cause rotation of the first member.

14. The apparatus of claim 13 wherein the second arm is pivotable relative to the first arm from the open position to the closed position.

15. The apparatus of claim 14 wherein the first member is rotatably coupled to the first arm, wherein the second member is rotatably coupled to the second arm.

16. The apparatus of claim 15 wherein the first member engages with the second member when the second arm is pivoted to the closed position, wherein rotation of the first member rotates the second member.

17. The apparatus of claim 15 wherein the rotatable assembly is operable to self-right the needle when the second arm is pivoted to the closed position.

18. The apparatus of claim 15 wherein the first member is coupled to a toggle, wherein the toggle is operable to rotate the first member.

19. The apparatus of claim 13 wherein the body portion comprises a toggle, wherein the toggle is operable to rotate the rotatable assembly relative to the first arm.

20. The apparatus of claim 19 wherein the second driving member comprises a control cable, wherein the toggle is coupled to the control cable, wherein the control cable is operable to rotate the rotatable assembly.

* * * * *